United States Patent [19]

Hansen et al.

[11] Patent Number: 5,543,215

[45] Date of Patent: *Aug. 6, 1996

[54] POLYMERIC BINDERS FOR BINDING PARTICLES TO FIBERS

[75] Inventors: Michael R. Hansen, Seattle; Richard H. Young, Sr., Renton, both of Wash.

[73] Assignee: Weyerhaeuser Company, Tacoma, Wash.

[ * ] Notice: The term of this patent shall not extend beyond the expiration date of Pat. No. 5,308,896.

[21] Appl. No.: 931,059

[22] Filed: Aug. 17, 1992

[51] Int. Cl.⁶ ................................................ B32B 5/16
[52] U.S. Cl. ........................ 428/283; 428/378; 428/393
[58] Field of Search ............................ 428/283, 378, 428/393; 264/109

[56] References Cited

U.S. PATENT DOCUMENTS

| | | | |
|---|---|---|---|
| 2,601,597 | 6/1952 | Daniel, Jr. et al. | 162/164.3 |
| 2,953,187 | 9/1960 | Francis, Jr. | 425/83.1 |

(List continued on next page.)

FOREIGN PATENT DOCUMENTS

| | | |
|---|---|---|
| 729513 | 6/1962 | Canada . |
| 806352 | 4/1964 | Canada . |
| 813616 | 12/1965 | Canada . |
| 841940 | 12/1965 | Canada . |
| 953890 | 9/1974 | Canada . |
| 1052156 | 12/1976 | Canada . |
| 0071063A1 | 2/1983 | European Pat. Off. . |
| 0096976A2 | 12/1983 | European Pat. Off. . |
| 122042 | 10/1984 | European Pat. Off. . |
| 0210754A1 | 2/1987 | European Pat. Off. . |
| 0429112A2 | 7/1989 | European Pat. Off. . |
| 0427316A2 | 7/1989 | European Pat. Off. . |
| 0427317A2 | 7/1989 | European Pat. Off. . |
| 0440472A1 | 1/1990 | European Pat. Off. . |
| 0442185A1 | 8/1991 | European Pat. Off. . |
| 0509708A1 | 10/1992 | European Pat. Off. . |
| 1382716 | 2/1964 | France . |
| 489308 | 1/1930 | Germany . |
| 1079796 | 6/1962 | Germany . |
| 2048721 | 6/1971 | Germany . |
| 2949531A1 | 7/1980 | Germany . |
| 61-28422 | 7/1986 | Japan . |
| 1217452 | 12/1969 | United Kingdom . |
| 2007998 | 5/1979 | United Kingdom . |
| 2092895 | 8/1982 | United Kingdom . |
| 2189127 | 10/1987 | United Kingdom . |
| WO88/01316 | 2/1988 | WIPO . |
| WO90/09236 | 8/1990 | WIPO . |
| WO90/11181 | 10/1990 | WIPO . |
| WO93/24153 | 12/1993 | WIPO . |
| WO94/04352 | 3/1994 | WIPO . |
| WO94/04351 | 3/1994 | WIPO . |
| WO95/00703 | 1/1995 | WIPO . |

OTHER PUBLICATIONS

Gugliemelli et al., "Base–Hydrolyzed Starch–Polyacrylonitrile (S–PAN) Graft Copolymer. S–PAN–1:1, PAN M.W. 794,000*," J. of Applied Copolymer Science, 13:2007–2017 (1969).

(List continued on next page.)

Primary Examiner—Christopher W. Raimund
Attorney, Agent, or Firm—Christensen O'Connor; Johnson & Kindness PLLC

[57] ABSTRACT

Particles are bound to fibrous material by a polymeric binder selected from the group consisting of poly(caprolactone) diol, polyamides and polyamines. The polymeric binder has a hydrogen bonding functionality or coordinate covalent bond forming functionality on each repeating unit of the polymeric binder. As a specific example, the fibrous material is cellulosic fibers and the particles are superabsorbent particles. Preferably 3–80 percent binder and 0.05–80 percent particles, by weight of the total weight of the fibrous material, binder and particles are included. The binder preferably has a molecular weight greater than 500 grams/mole, preferably 4,000–8,000 grams/mole. Particles attached to the fibers in this manner are firmly adhered and are not easily dislodged. Fibrous products produced by this method include fibers to which particles are bound, and fibers which have been treated with the binder but to which particles are not bound.

61 Claims, 6 Drawing Sheets

U.S. PATENT DOCUMENTS

| | | | |
|---|---|---|---|
| 3,010,161 | 11/1961 | Duvall | 264/116 |
| 3,021,242 | 12/1962 | Touey | 156/180 |
| 3,059,313 | 10/1962 | Harmon | 28/80 |
| 3,070,095 | 12/1962 | Torr | 328/284 |
| 3,087,833 | 4/1963 | Drelich | 117/38 |
| 3,327,708 | 6/1967 | Sokolowski | 128/156 |
| 3,344,789 | 10/1967 | Arnold et al. | 128/287 |
| 3,377,302 | 4/1968 | Gugliemelli et al. | 260/17.4 |
| 3,395,201 | 7/1968 | Kalwaites | 264/45 |
| 3,425,971 | 2/1969 | Gugliemelli et al. | 260/17.4 |
| 3,494,992 | 2/1970 | Wiegand | 264/121 |
| 3,521,638 | 7/1970 | Parrish | 128/284 |
| 3,554,788 | 1/1971 | Fechillas | 117/140 |
| 3,661,154 | 5/1972 | Torr | 128/284 |
| 3,661,632 | 5/1972 | Gagliardi et al. | 117/143 |
| 3,669,103 | 6/1972 | Harper et al. | 128/156 |
| 3,670,731 | 6/1972 | Harmon | 128/284 |
| 3,672,945 | 6/1972 | Taylor | 117/100 |
| 3,692,622 | 9/1972 | Dunning | 161/124 |
| 3,745,060 | 7/1973 | Jumentier et al. | 161/170 |
| 3,758,641 | 11/1973 | Zweigle | |
| 3,766,922 | 10/1973 | Krusko | 128/284 |
| 3,777,758 | 12/1973 | Mesek et al. | 128/284 |
| 3,788,936 | 1/1974 | Brock et al. | 161/148 |
| 3,804,092 | 4/1974 | Tunc | 128/284 |
| 3,808,088 | 4/1974 | Knechtges et al. | 161/148 |
| 3,886,941 | 6/1975 | Duane et al. | 128/287 |
| 3,888,256 | 6/1975 | Studinger | 128/296 |
| 3,888,257 | 6/1975 | Cook et al. | 128/296 |
| 3,901,236 | 9/1975 | Assarsson et al. | 128/284 |
| 3,903,889 | 9/1975 | Torr | 128/287 |
| 3,908,659 | 9/1975 | Wehrmeyer et al. | 128/287 |
| 3,923,592 | 12/1975 | George et al. | 162/168 |
| 3,949,035 | 4/1976 | Dunning et al. | 264/90 |
| 3,978,257 | 8/1976 | Ring | 428/137 |
| 3,991,237 | 11/1976 | Topfl et al. | 427/386 |
| 4,007,083 | 2/1977 | Ring et al. | 162/101 |
| 4,009,313 | 2/1977 | Crawford et al. | 428/290 |
| 4,035,217 | 7/1977 | Kennette et al. | 156/279 |
| 4,055,180 | 10/1977 | Karami | 128/287 |
| 4,061,268 | 12/1977 | DeMaster | 238/14 |
| 4,062,451 | 12/1977 | Gander | 206/524.2 |
| 4,071,636 | 1/1978 | Nishino et al. | 427/2 |
| 4,102,340 | 7/1978 | Mesek et al. | 128/287 |
| 4,103,062 | 7/1978 | Aberson et al. | 428/283 |
| 4,160,059 | 7/1979 | Samejima | 428/288 |
| 4,232,674 | 11/1980 | Melican | 128/287 |
| 4,250,660 | 2/1981 | Kitamura et al. | 47/57.6 |
| 4,282,121 | 8/1981 | Goodrich | 260/17.4 |
| 4,289,513 | 9/1981 | Brownhill et al. | 55/387 |
| 4,289,536 | 9/1981 | Dereser | 106/99 |
| 4,324,706 | 4/1982 | Tabe et al. | 523/149 |
| 4,332,917 | 5/1982 | Heslinga et al. | |
| 4,338,417 | 7/1982 | Heslinga et al. | |
| 4,364,992 | 12/1982 | Ito et al. | 428/283 |
| 4,379,194 | 4/1983 | Clarke et al. | 428/203 |
| 4,394,172 | 7/1983 | Scheuble et al. | 106/38.5 |
| 4,404,250 | 9/1983 | Clarke | 428/220 |
| 4,410,571 | 10/1983 | Korpman | 427/385 |
| 4,412,036 | 10/1983 | Pederson et al. | 525/54.26 |
| 4,424,247 | 1/1984 | Erickson | 428/138 |
| 4,457,978 | 7/1984 | Wawzonek | 524/14 |
| 4,467,012 | 8/1984 | Pederson et al. | 428/248 |
| 4,486,501 | 12/1984 | Holbek | 428/375 |
| 4,492,729 | 1/1985 | Bannerman et al. | 428/283 |
| 4,532,176 | 7/1985 | Briggs et al. | 428/288 |
| 4,537,767 | 8/1985 | Rothman et al. | 424/78 |
| 4,558,091 | 12/1985 | Hubbard | 524/734 |
| 4,597,930 | 7/1986 | Szal | 264/115 |
| 4,673,402 | 6/1987 | Weisman et al. | 604/368 |
| 4,676,784 | 6/1987 | Erdman et al. | 604/368 |
| 4,758,466 | 7/1988 | Dabi et al. | 428/283 |
| 4,772,492 | 9/1988 | Bouchette | 427/342 |
| 4,788,080 | 11/1988 | Hojo et al. | 427/204 |
| 4,818,599 | 4/1989 | Marcus | 428/288 |
| 4,826,880 | 5/1989 | Lesniak et al. | 521/53 |
| 4,833,011 | 5/1989 | Horimoto | 428/288 |
| 4,842,593 | 7/1989 | Jordan et al. | 604/360 |
| 4,874,811 | 10/1989 | Borchers et al. | 524/516 |
| 4,886,697 | 12/1989 | Perdelwitz, Jr. et al. | 428/192 |
| 4,892,769 | 1/1990 | Perdelwitz, Jr. et al. | 428/68 |
| 4,902,565 | 2/1990 | Brook | 428/315.5 |
| 4,964,954 | 10/1990 | Johansson | 162/164.6 |
| 5,002,814 | 3/1991 | Knack et al. | 428/85 |
| 5,057,166 | 10/1991 | Young, Sr. et al. | 156/62.2 |
| 5,064,689 | 11/1991 | Young, Sr. et al. | 427/202 |
| 5,128,082 | 7/1992 | Makoui | 264/112 |
| 5,161,686 | 11/1992 | Weber et al. | 206/440 |
| 5,217,445 | 6/1993 | Young et al. | 604/381 |
| 5,225,047 | 7/1993 | Graef et al. | 162/9 |
| 5,230,959 | 7/1993 | Young, Sr. et al. | 428/372 |
| 5,252,275 | 10/1993 | Sultze et al. | 264/119 |
| 5,252,340 | 10/1993 | Honeycutt | 424/489 |
| 5,278,222 | 1/1994 | Stack | 525/502 |
| 5,283,123 | 2/1994 | Carter et al. | 428/403 |
| 5,300,054 | 4/1994 | Feist et al. | 604/378 |
| 5,300,192 | 4/1994 | Hansen et al. | 162/184 |
| 5,308,893 | 5/1994 | Hansen et al. | 524/13 |
| 5,308,896 | 5/1994 | Hansen et al. | |
| 5,312,522 | 5/1994 | Van Phan et al. | 162/111 |
| 5,352,480 | 10/1994 | Hansen et al. | |
| 5,362,776 | 11/1994 | Barenberg et al. | |
| 5,447,977 | 9/1995 | Hansen et al. | |

OTHER PUBLICATIONS

Weaver et al., "Hydrolyzed Starch–Polyacrylonitrile Graft Copolymers: Effect of Structure on Properites*," J. of Applied Polymer Science, 15:3015–3024 (1971).

Weaver et al., "Highly Absorbent Starch–Based Polymer," Northern Regional Research Laboratory, Agricultural Research Service, U.S. Dept. of Agriculture, Peoria, Illinois, pp. 169–177.

"Super slurpers: Time for change?," Chemical Week, pp. 21–22 (Jul. 24, 1974).

Lindsay, "Absorbent Starch Based Co–polymers—Their Characteristics and Applications," Formed Fabrics Industry, pp. 20, 24 and 26 (May 1977).

Burkholder, "Absorbent Polymers—A New Concept in Fluid Absorption," The Dow Chemical Company Designed Products Laboratory, Midland, Michigan, pp. 73–79 (1973).

Lysogorskaya et al., "Effect of Moisture Content on the Development of Interfiber Bonds in Air–Laid Paper," Leningrad Technological Institute of the Pulp and Paper Industry, Zh. Prikl. Khim., 63:(8) 1869–1872 (1990).

Ogurtsov et al., "Effect of the modulus of elasticity of the binder on the properties of dry–process paper," Sb. Tr. Tsentr. Nauch.–Issled. Inst. Bumagi, 9:123–127 (1974).

Amosov, et al., "Aluminum hydroxy compounds—binders for dry–process paper," Izv. VUZ, Lesnoi Zh., 6:72–76 (1986).

Gorbushin et al., "Investigation of the effect of the nature and concentration of binders on the properties of dry–process paper," Sb. Tr. Tsentr. Nauch.–Issled. Inst. Bumagi, 9:117–123 (1974).

Hogue et al., "Granulation and Tabletting of Iron Oxide–Chromic Oxide Catalyst Mass With the Aid of Binding Ingredients Part II–Cellulosic Derivatives and Polyethylene Glycol as Binding Ingredients," Fertilizer Technology, 20:30–35 (1983).

Lsysogorskaya et al., "Effect of Moisture Content on Development of Interfiber Bonding in the Structure of Air–Dried Paper," Plenum Publ. Corp., pp. 1730–1733 (1991).

Sliwiok an Kowalska, "Investigation of Self–Association of the Selected Glycols on Cellulose Sorbents," Microchemical Journal, 26:68–74 (1981).

Blanchard and Reinhart, "Dyeing of Crosslinked Cotton Containing Glycol Additives," U.S. Dept. of Agriculture, New Orleans, 24:13–17 (Jan. 1992).

Byrd, "How bonds develop during web consolidation," PTI, pp. 240–243 (Oct. 1986).

S. Lammie, "Use of Glycerine as a Softener for Paper Products," The World's Paper Trade Review, Dec. 13, 1962, p. 2050.

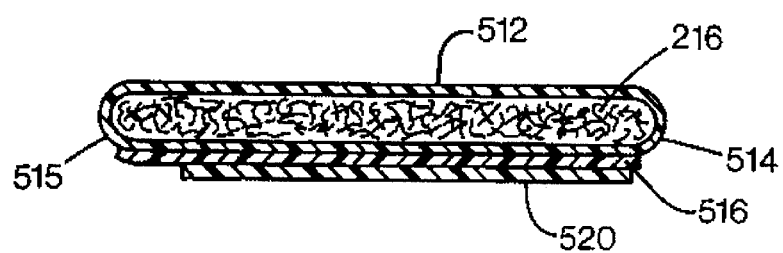
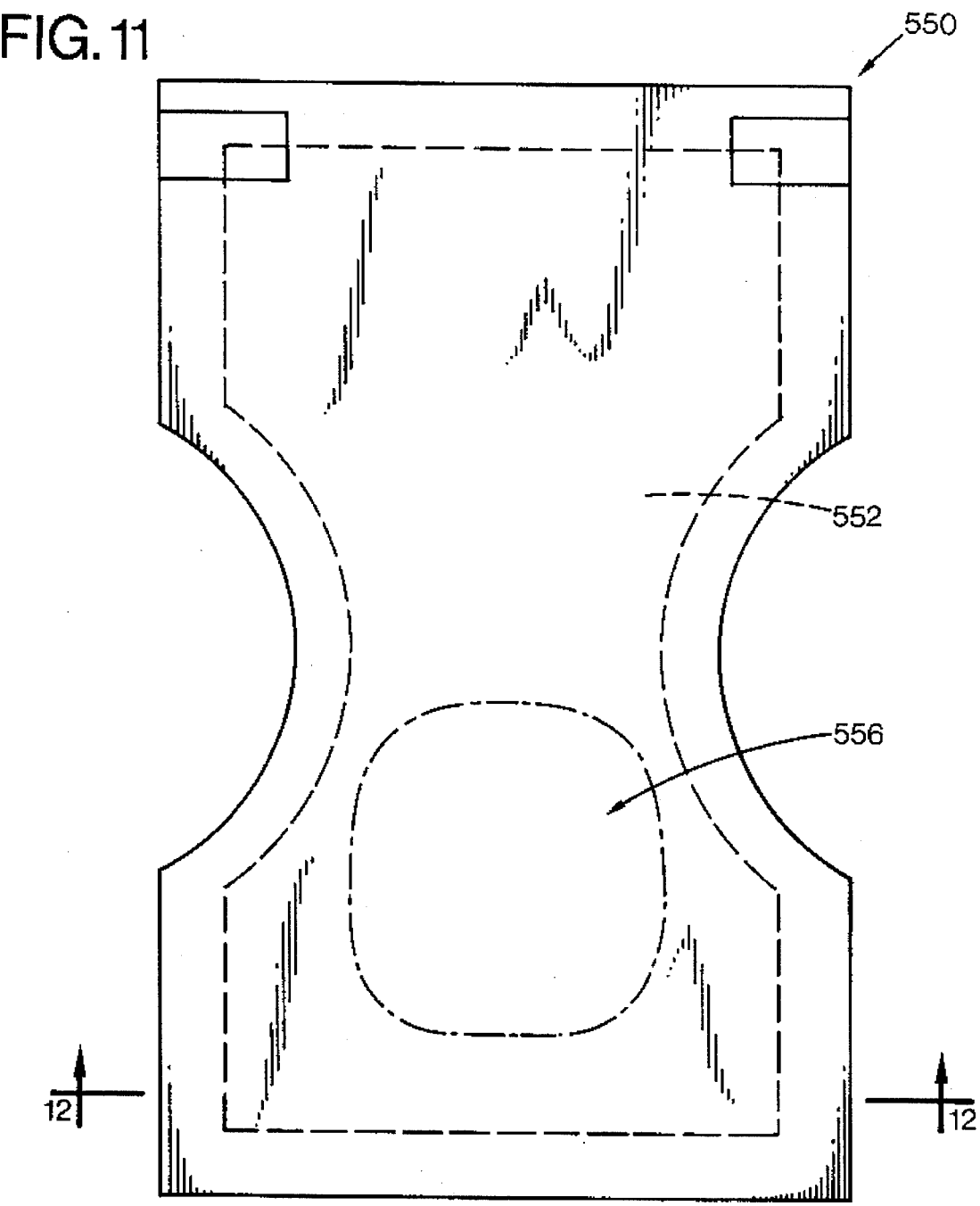

FIG. 12
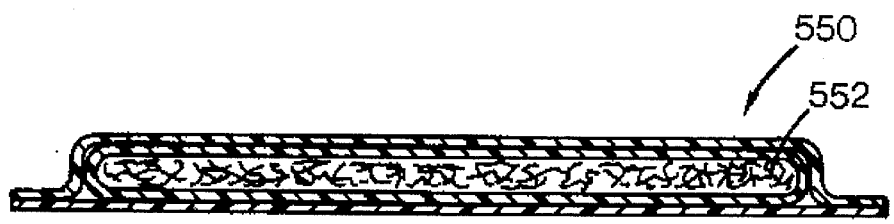
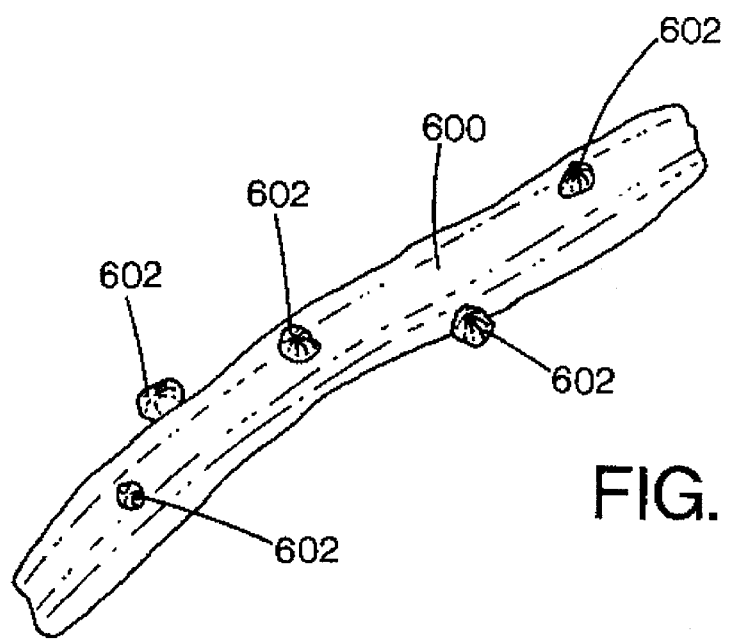
FIG. 13
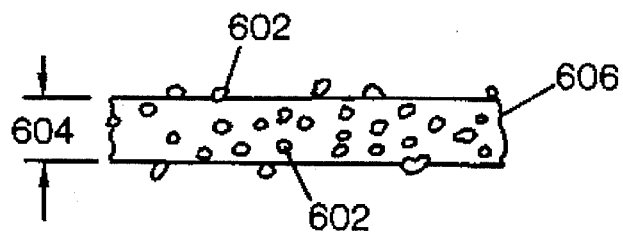
FIG. 14

POLYMERIC BINDERS FOR BINDING PARTICLES TO FIBERS

BACKGROUND OF THE INVENTION

1. Field of the Invention

This invention concerns polymeric binders for fibers and the use of such binders in binding particles to fibers. In particular embodiments, it concerns binding superabsorbent particles to cellulosic fibers which may then be used, for example, to make absorbent fibers that are incorporated into cellulosic products.

2. General Discussion of the Background

Superabsorbent polymers have been developed in recent years that are capable of absorbing many times their own weight of liquid. These polymers, which are also known as water insoluble hydrogels, have been used to increase the absorbency of sanitary products such as diapers and sanitary napkins. Superabsorbent polymers are often provided in the form of particulate powders, granules, or fibers that are distributed throughout absorbent cellulosic products to increase the absorbency of the product. Superabsorbent particles are described, for example, in U.S. Pat. Nos. 4,160,059; 4,676,784; 4,673,402; 5,002,814; and 5,057,166. Products such as diapers that incorporate absorbent hydrogels are shown in U.S. Pat. Nos. 3,669,103 and 3,670,731.

One problem with the use of superabsorbents is that the superabsorbent material can be physically dislodged from the cellulosic fibers of an absorbent product. Separation of the superabsorbent from its substrate reduces the absorbency of the product and diminishes the effectiveness of the superabsorbent material. This problem was addressed in European Patent Application 442 185 A1, which discloses use of a polyaluminum chloride binder to bind an absorbent polymer to a fibrous substrate. The polyaluminum binder, however, suffers from the drawback of being an inorganic product that is not readily biodegradable. Moreover, that European patent does not offer any guidance for selecting binders other than polyaluminum chloride that would be useful in binding absorbent particles.

A method of immobilizing superabsorbents is disclosed in U.S. Pat. No. 4,410,571 in which a water swellable absorbent polymer is converted to a non-particulate immobilized confluent layer. Polymer particles are converted to a coated film by plasticizing them in a polyhydroxy organic compound such as glycerol, ethylene glycol, or propylene glycol. The superabsorbent assumes a non-particulate immobilized form that can be foamed onto a substrate. The individual particulate identity of the superabsorbent polymer is lost in this process. The confluent nature of the superabsorbent material can also result in gel blocking, in which absorption is diminished as the water swollen polymers block liquid passage through the film layer.

U.S. Pat. Nos. 4,412,036 and 4,467,012 disclose absorbent laminates in which a hydrolyzed starch polyacrylonitrile graft copolymer and glycerol mixture is laminated between two tissue layers. The tissue layers are laminated to each other by applying external heat and pressure. The reaction conditions form covalent bonds between the tissue layers that firmly adhere the tissue layers to one another.

Numerous other patents have described methods of applying binders to fibrous webs. Examples include U.S. Pat. Nos. 2,757,150; 4,584,357; and 4,600,462. Such binders are not described as being useful in binding particulates, such as superabsorbent particles, to fibers. Yet other patents disclose crosslinking agents such as polycarboxylic acids that form covalent intrafiber bonds with individualized cellulose fibers, as in European Patent Application 440472 A1; European Patent Application 427 317 A2; European Patent Application 427 316 A2; and European Patent Application 429 112 A2. The covalent intrafiber bonds are formed at elevated temperatures and increase the bulk of cellulose fibers treated with the crosslinker. The covalent bonds between the fibers produce a pulp sheet that is more difficult to compress to conventional pulp sheet densities than in an untreated sheet. Any covalent crosslink bonds that form between the fibers and particles occupy functional groups that would otherwise be available for absorption, hence absorption efficiency is decreased.

It is an object of this invention to provide an improved method of binding particulates, such as superabsorbent particles, to fibers.

It is another object to provide an improved method of binding particulates such that they can be distributed throughout a fibrous product without necessarily being confined to the surface of a product.

Another object of the invention is to provide improved fiber and absorbent products in which particulates are firmly bound to cellulose fibers such that the particles are less likely dislodged by mechanical forces.

Yet another object of the invention is to provide an improved particle binder that is environmentally compatible and easily biodegradable.

Even yet another object is to provide such a product that has improved processing characteristics, such as ease of densification.

Finally, it is an object of the invention to bind a broad variety of particles to many different kinds of fibers using an improved, simple and versatile binding process.

SUMMARY OF THE INVENTION

The foregoing and other objects are achieved by providing fibers that have particles bound to the fibers with a polymeric binder. The binder is selected from the group consisting of a polypropylene glycol, a polypropylene glycol/polyethylene glycol copolymer, polyacrylic acid, a poly(caprolactone) diol, a polyamide and a polyamine, wherein the polymeric binder has a hydrogen bonding functionality or coordinate covalent bond forming functionality on each repeating unit of the polymeric binder. The fibrous material may be cellulosic or synthetic fibers that are capable of forming hydrogen bonds with the binder, while the particles are selected to be of the type which form hydrogen bonds or coordinate covalent bonds with the binder. It has unexpectedly been found that this binder system secures particles to fibers exceptionally well. A superior fibrous product is therefore produced which has improved absorbent properties as compared to unbound or covalently bound particles. The noncovalent bond also produces a product that is more easily manufactured and densified, and that is more readily biodegradable and disposable.

In one preferred embodiment, an absorbent product is comprised of a fibrous cellulosic mat that contains superabsorbent hydrogel particles in particulate form. The superabsorbent particles form hydrogen bonds or coordinate covalent bonds with the binder, depending upon the binder, while the binder in turn forms hydrogen bonds with the hydroxyl groups of the cellulose fibers. These noncovalent, relatively flexible bonds between the binder and particles maintain the particles in contact with the fibers, and resist dislodgement of the particles by mechanical forces applied to the mat during manufacture, storage or use. The binder may suitably be present in an amount of from about 3 to 80 percent of the total weight of the product, while the particles bound by the binder of the present invention (via hydrogen/ coordinate covalent bonds) may suitably be present in an amount of 0.05 to 80 percent, preferably 1 to 80 percent or 5 to 80 percent by weight. An especially suitable range of binder is 3 to 40 percent by weight, or 3 to 25 percent by weight, while a particularly suitable range of such particles is 5 to 40 percent by weight. A preferred weight ratio of particle to binder is 2:1 to 4:1. An example of a suitable particle is a superabsorbent polymer such as a starch graft polyacrylate hydrogel fine or larger size particle such as a granule, which forms hydrogen bonds with the binder. The binder also forms hydrogen bonds with the hydroxyl groups of the cellulose, thereby securely attaching the superabsorbent particles to the fibers.

The present invention also includes a method of binding particles to fibers wherein the particles are insoluble in the binder and therefore retain their solid particulate form following binding. The particles have functional groups that can form hydrogen bonds or coordinate covalent bonds with the binder, and the binder in turn is capable of forming hydrogen bonds to the fibers. The binder is either polypropylene glycol, polyacrylic acid, poly(caprolactone) diol, a polyamide (such as a polypeptide) or a polyamine wherein there is a hydrogen bonding functionality or coordinate covalent bond forming functionality on each repeating unit of the polymer. In especially preferred embodiments, the fibers are cellulosic and the particles are superabsorbent particles that are bound to the binder by hydrogen bonds. The fibers may also be continuous or discontinuous synthetic or natural fibers having a hydrogen bonding functional group that hydrogen bonds the binder.

In a particular embodiment (without limitation), the polymer may suitably have a molecular weight greater than 500 grams/mole, more suitably greater than 4000 grams/mole and less than 8000 grams/mole. The binder may be applied to the fiber product, for example by spraying, slurrying, roll coating, or otherwise in an amount of at least 3 percent by weight, and suitably no more than 70 percent by weight. The particles may be placed in contact with the fibers either before or after the binder is applied, and the binding reaction occurs at a temperature below 150° C., suitably without external application of heat at ambient temperature (e.g. about 25° C.). Particles may also be bound in the absence of any external application of pressure, or in the absence of external heat and pressure.

The binder may be either a solid binder such as a high molecular weight polypropylene glycol (PPG), a PPG/PEG copolymer, or polyacrylic acid; or a liquid binder such as a low molecular weight PPG (less than 4000 grams/mole) or a hot melt of any of the solid binders. When a solid binder (for example, a dry powder or a dried liquid) is used, the fibers suitably contain at least 7 percent water by weight when the binding of particles to fibers occurs. This level of moisture in the fibers provides sufficient mobility of reactants to allow the particles and fibers to bind well to each other. When a liquid binder is used (for example, PPG or a solution of polyacrylic acid), the fibers suitably initially contain at least about 0.5 percent water by weight before the liquid binder is added. A solid binder is suitably used with fibers having 0.5 percent water by weight if the binder is heated above its melting point to liquefy it. The solid binder may be thermoplastic or meltable, such that it can be heated above its melting point to soften the binder and then cooled to fuse fibers to each other. The thermoplastic properties of the binder can also provide mechanical encapsulation that helps maintain the particles and fibers together.

An auxiliary binder may also be used to help bind fibers to each other. The auxiliary binder may be a solid thermoplastic material other than the polymeric binder that is applied to the fibers and softened by elevating the temperature during the binding step to above the softening temperature of the auxiliary binder. The auxiliary binder is thereby temporarily softened (which, for purposes of convenience, may be referred to as auxiliary binder melting) and subsequently resolidified as the temperature cools, which thermoplastically binds the fibers to each other, and the particles to the fibers. Alternatively, the auxiliary binder may be a thermosetting material that is activated by heating to a specified temperature at which the thermosetting material then binds fibers to each other, and the particles to the fibers. The auxiliary binder may also contain a hydrogen bonding functionality that hydrogen bonds the particle to the fiber. Examples of auxiliary binders that are thermoplastic and also contain hydrogen bonding groups include ethylene vinyl alcohol, polyvinyl acetate, acrylates, polycarbonates, polyesters and polyamides. Further information about the use of such thermoplastic binders can be found in U.S. Pat. No. 5,057,166, which is incorporated herein by reference.

In some embodiments, the particles are bonded to the fibers in the absence of substantial intrafiber bonding, such as the intrafiber crosslinking that occurs with individualized cellulose fibers that are exposed to polycarboxylic acid crosslinkers at elevated curing temperatures. In other embodiments, particles are bound to fibers that have intrafiber bonding, such as the high bulk additive intrafiber crosslinked cellulose fibers disclosed in U.S. patent application Ser. No. 07/607,268 filed Oct. 31, 1990, and in European Patent Applications 440 472 A1 and 427 317 A2. The fibrous product of the present invention (with or without substantial intrafiber crosslinking) may be densified by external application of pressure. The densified product is compact, easily transported, and has superior absorbent properties as compared to nondensified products. The present inventors have found that the binders of the present invention produce a product that can be easily densified with reduced application of external pressure as compared to products that do not use the binders of the present invention. Either liquid or solid binders provide enhanced densification, but solid binders are most preferably moistened or otherwise fluidized to provide this benefit.

In some particular embodiments, the method produces a cellulosic fiber composite mat in which absorbent particles are bound to the fibers with a binder in the absence of the external application of heat. The binder is either polypropylene glycol, A PPG/PEG copolymer, polyacrylic acid, a polyamide, a polyamine or combinations thereof, that has a hydrogen bonding functionality on each repeating unit of the polymer and most preferably has a molecular weight greater than 500 grams/mole. The binder is applied in an amount of 3–80 percent by weight of the fiber product, and is preferably used to bind superabsorbent or other particles with the requisite functionality groups to the mat.

The foregoing and other features and advantages of the invention will become more apparent from the following detailed description and accompanying drawings.

BRIEF DESCRIPTION OF THE DRAWINGS

FIG. 10 is a sectional view of the appliance of FIG. 9 taken along line 10—10 of FIG. 9.

FIG. 11 is a plan view of a disposable diaper including a core of fibers of the present invention.

FIG. 12 is a vertical sectional view of the diaper of FIG. 11.

FIG. 13 is a view of an enlarged fiber with particles bonded to the fiber with the binders of the present invention.

FIG. 14 is a schematic view of a cellulose mat with particles bound to all its surfaces and throughout its depth.

DETAILED DESCRIPTION OF SEVERAL PREFERRED EMBODIMENTS OF THE INVENTION

Fiber Characteristics

Figure 1:
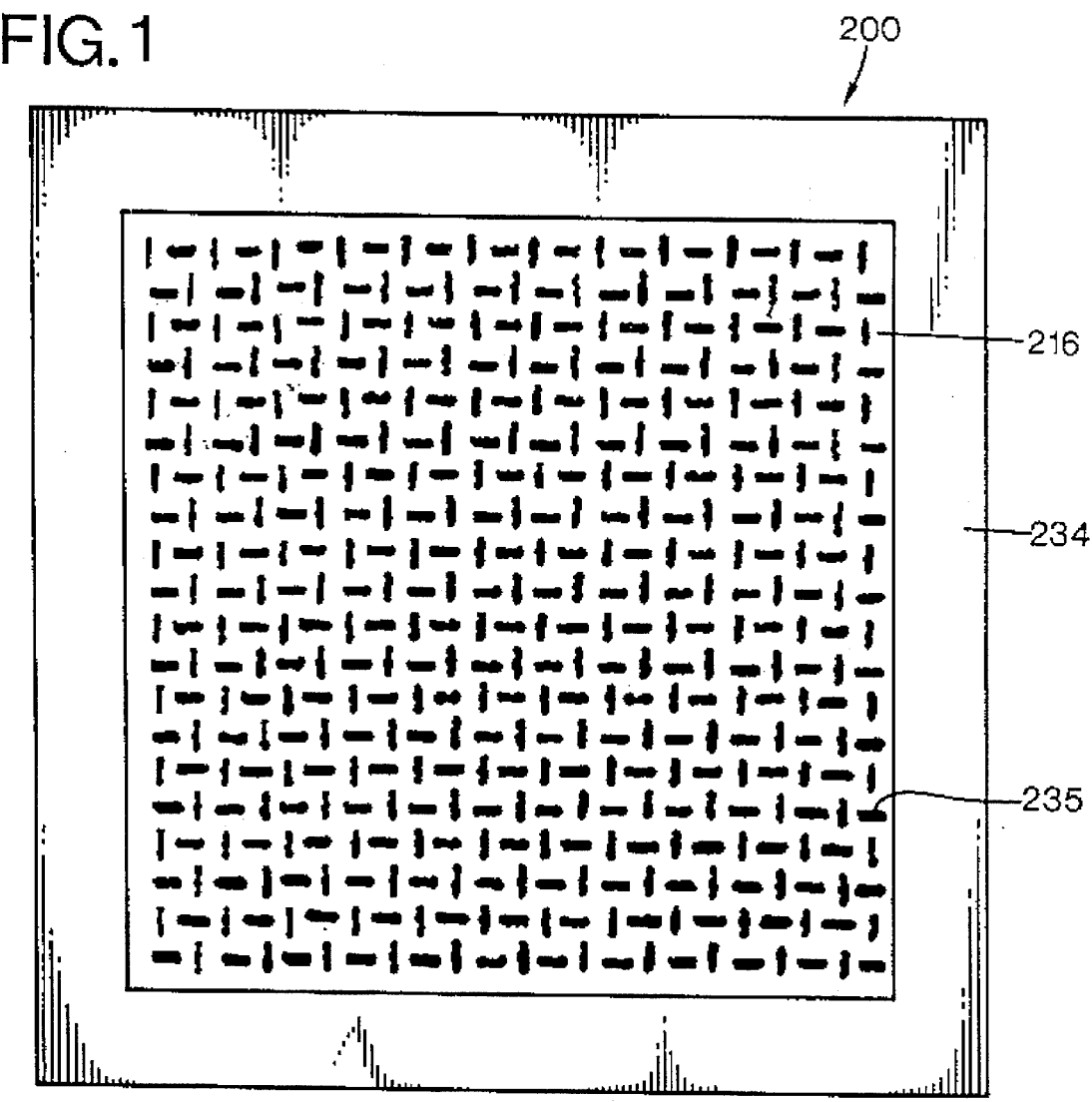
FIG. 1 is a top plan view of a structure into which fibers of the present invention are incorporated with attached particles, the fibers being in the form of an illustrated absorbent pad.

The present invention includes a method of binding particles to fibers, and the product produced by that method. In particularly preferred embodiments, the product is a cellulosic or synthetic fiber to which superabsorbent hydrogel polymer particles are adhered by a binder, and absorbent products made therefrom. Suitable fibers include wood pulp fibers, which can be obtained from well known chemical processes such as the kraft and sulfite processes. In these processes, the best starting material is prepared from long fiber coniferous wood species, such as pine, Douglas fir, spruce and hemlock. Wood pulp fibers can also be obtained from mechanical processes, such as ground wood, mechanical, thermomechanical, chemimechanical, and chemithermomechanical pulp processes. The fibers are preferably elongated, for example having a length to width ratio of about 10:1 or 5:1.

The fibers of the present invention also include fibers that are pretreated prior to the application of a binder to the fibers as explained below. This pretreatment may include physical treatment, such as subjecting the fibers to steam or chemical treatment, such as cross-linking the fibers. Although not to be construed as a limitation, examples of pretreating fibers include the application of fire retardants to the fibers, such as by spraying the fibers with fire retardant chemicals. Specific fire retardant chemicals include, by way of example, sodium borate/boric acid, urea, urea/phosphates, etc. In addition, the fibers may be pretreated with surfactants or other liquids, such as water or solvents, which modify the surface of the fibers. Other pretreatments include exposure to antimicrobials or pigments.

The fibers may also be pretreated in a way which increases their wettability. For example, natural fibers may be pretreated with a liquid sodium silicate, as by spraying the fibers with this material, for pretreatment purposes. Wettability of the surface of fibers is also improved by subjecting the fibers to a corona discharge pretreatment in which electrical current is discharged through the fibers in a conventional manner. In the case of both synthetic fibers and wood pulp fibers, corona discharge pretreatment results in an oxygen functionality on the surface of the fibers, making them more wettable and more bondable. The fibers may also be pretreated with conventional cross-linking materials and may be twisted or crimped, as desired. Pretreating cellulose fibers with chemicals which result in lignin or cellulose rich fiber surfaces may also be performed in a conventional manner.

Bleaching processes, such as chlorine or ozone/oxygen bleaching may also be used in pretreating the fibers. In addition, the fibers may be pretreated, as by slurrying the fibers in baths containing antimicrobial solutions (such as solutions of antimicrobial particles as set forth below), fertilizers and pesticides, and/or fragrances and flavors, for release over time during the life of the fibers. Fibers pretreated with other chemicals, such as thermoplastic and thermoset resins may also be used. Combinations of pretreatments may also be employed with the resulting pretreated fibers then being subjected to the application of the binder coating as explained below.

Ground wood fibers, recycled or secondary wood pulp fibers, and bleached and unbleached wood pulp fibers can be used. Details of the production of wood pulp fibers are well known to those skilled in the art. These fibers are commercially available from a number of companies, including Weyerhaeuser Company, the assignee of the present invention.

The fibers can also be any of a variety of other natural or synthetic fibers, however, all of the fibers to which particles are attached in accordance with the present invention must include a hydrogen bonding functionality. This does not preclude the blending of such fibers with fibers lacking this characteristic. However, the fibers lacking a hydrogen bonding functionality will not have particles bonded thereto with the strength of the bonds that would be present if the fibers had a hydrogen bonding functionality.

A hydrogen bond is an intermolecular force that occurs between hydrogen atoms that are covalently bonded to small, strongly electronegative elements (such as nitrogen and oxygen) and nonbonding electron pairs on other such electronegative elements. A hydrogen bonding functionality is a functional group that contains an oxygen or nitrogen atom, for example hydroxyls, carboxyls, ethers, esters, epoxides, carbonyls, amines, urethanes and others, that is capable of forming a hydrogen bond. The orbitals of the nonbonding electron pairs on the oxygen or nitrogen overlap with the relatively empty 1s orbital of the hydrogen covalently bonded to another nitrogen or oxygen atom. The 1s orbital of the hydrogen is relatively empty due to the unequal sharing of the electrons in the covalent bond between it and the small electronegative atom (oxygen or nitrogen) to which it is bound.

Specific examples of natural fibers that contain a hydrogen bonding functionality include chopped silk fibers, wood pulp fibers, bagasse, hemp, jute, rice, wheat, bamboo, corn, sisal, cotton, flax, kenaf, peat moss, and mixtures thereof.

Suitable synthetic fibers with hydrogen bonding functionalities include acrylic, polyester, carboxylated polyolefins, rayon and nylon. The hydrogen bonding functionality is an ester in acrylic fibers and a carboxylic acid in carboxylated polyolefin fibers, an ester in polyester, an amide in nylon, and a hydroxyl in rayon. Polyethylene and polypropylene would be unsuitable fibers for use in particle to fiber bonding in accordance with the present invention because they include only carbons and hydrogens without any oxygens or nitrogens that can participate in hydrogen bonds.

For purposes of convenience, and not to be construed as a limitation, the following description proceeds with reference to the treatment of individual chemical wood pulp fibers. The fibers are individualized, for example by defiberization in a hammermill. Such individualized fibers are conventionally formed into a mat, and are commercially available, for example as NB 416 from the Weyerhaeuser Company. Another suitable cellulosic mat would include Rayfloc JLD from ITT Rayonier. The cellulose fibers may be in the form of a cellulosic web or loose cellulose fibers.

Particle Characteristics

In accordance with the present invention, particles are added to the mat to give it desired properties, such as increased absorbency, abrasiveness, or antimicrobial activity. The particle can be any particulate material that has the desired property and which is capable of forming hydrogen bonds or coordinate covalent bonds with the binder. Hydrogen bonds can be formed, as discussed above, by particles that contain functional groups having an oxygen or nitrogen. Coordinate covalent bonds, in contrast, are formed by donation of a lone pair of electrons on one atom to an empty orbital of another atom. Coordinate covalent bonds differ from covalent bonds in that covalent bonds are formed by a pair of electrons wherein one of the electrons is donated from each of the atoms that participate in the bond. Particles can form coordinate covalent bonds if they have an empty p or d or f orbital that is capable of accepting a pair of electrons from the binder.

A coordinate covalent bond occurs between a donor compound that has a lone pair of electrons to donate to the bond, and an acceptor that has an empty orbital to accept the lone pair of electrons from the donor. According to the Aufbau and Pauli principles, electrons occupy the lobes of atomic orbitals one at a time with a maximum of two electrons (with opposite spins) per lobe. The most basic orbital is the s orbital, which is available for bonding the elements in the first row of the periodic table. In the second row of the periodic table, electrons fill first the 2s orbital of Li and Be, but metals in Groups IA and IIA do not have sufficient affinity for electrons to participate in coordinate covalent bonding. Beginning with column IIIA (boron), the three p orbitals participate in coordinate covalent bonding and the lobes of the p orbitals begin to fill. Boron has one electron in one of the 2p orbitals thus leaving the other two p orbitals empty and available for coordinate covalent bonding. An example of a coordinate covalently bonded boron containing particle is boric acid, which is used as an astringent, antiseptic and fire retardant.

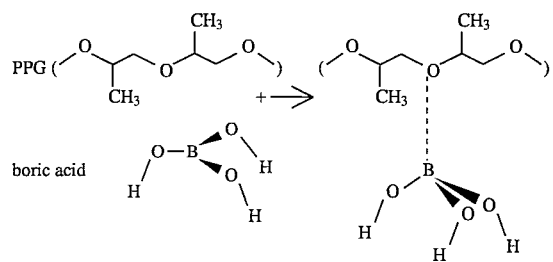

The next element, carbon, usually hybridizes to have one electron in the 2s orbital and the three remaining electrons are singly placed in the three p orbitals. This leaves no lobes empty for coordinate covalent bonding and electron additions proceeding further across that row of the periodic table also leave no lobes empty. Hence, boron is the only element in the second row of the periodic table that is capable of forming coordinate covalent bonds.

Next the third row begins to fill, and the two 3s electrons fill first in sodium and magnesium, but these metals in groups IA and IIA do not form coordinate covalent bonds as discussed above. Then aluminum, like boron, places one electron in one of the 3p lobes, and the two other 3p lobes are empty and available for coordinate covalent bonding. The same trends continue across the third row, but the third row elements also have available five 3d lobes so the potential for coordination bonding exists even though 3p orbitals are occupied in the third row. Hence, Al, P, S, and Cl are capable of accepting a pair of electrons from an electron pair donor to form a coordinate covalent bond. An example of this is found in the bonding in PCl$_5$, aluminum trihydrate, or phosphorous pentasulfide. A phosphorous pentasulfide particle can be used to increase flammability of a product, while aluminum trihydrate is a fire retardant. An example of a coordinate covalently bonded aluminum compound is

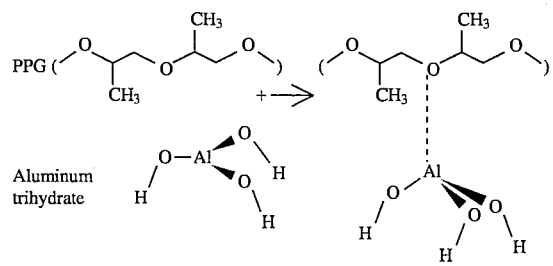

wherein aluminum trihydrate is coordinate covalently bonded to a polypropylene glycol polymer.

In the next row, the 4s orbital is filled first, then the 3d lobes begin to fill—one electron per lobe until all have a single then a second electron to each lobe until all lobes are filled. However, 4p and 4f orbitals are also available, so many of the transition elements are capable of forming coordinate covalent bonds.

The elements that have empty orbitals that participate in coordinate covalent bonding include all those except the metals (which excludes hydrogen) in groups IA and IIA, and C, N, O, F, Ne and He. Preferred particles contain boron, aluminum, iron, rhodium, osmium, platinum, and palladium, particularly boron. Particles in accordance with this invention that are capable of coordinate covalent bonding are aluminum trihydrate, antimony oxide, arsenic disulfide, bismuth aluminate, bismuth iodide oxide, bismuth phosphate, bismuth subcarbonate, bismuth subgallate, cadmium salycilate, chromic carbonate, chromic hydroxide, chromic oxide, and chromic phosphate. All of the polymeric binders of the present invention (PPG, PAA, poly(caprolactone) diol, polyamide and polyamine) are capable of donating a lone pair of electrons from an oxygen or nitrogen to form a coordinate covalent bond with a suitable particle that has an empty orbital for coordinate covalent bonding.

Superabsorbent Particles

In one disclosed embodiment the added particles are superabsorbent particles, which comprise polymers that swell on exposure to water and form a hydrated gel (hydrogel) by absorbing large amounts of water. Superabsorbents are defined herein as materials that exhibit the ability to absorb large quantities of liquid, i.e. in excess of 10 to 15 parts of liquid per part thereof. These superabsorbent materials generally fall into three classes, namely starch graft copolymers, crosslinked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-crosslinking polyacrylic acid, a crosslinked polyacrylate salt, carboxylated cellulose, and a neutralized crosslinked isobutylene-maleic anhydride copolymer.

Superabsorbent particles are available commercially, for example starch graft polyacrylate hydrogel fines (IM 1000F) from Hoechst-Celanese of Portsmouth, Va., or larger particles such as granules. Other superabsorbent particles are marketed under the trademarks SANWET (supplied by Sanyo Kasei Kogyo Kabushiki Kaisha), SUMIKA GEL (supplied by Sumitomo Kagaku Kabushiki Kaisha and which is emulsion polymerized and spherical as opposed to solution polymerized ground particles), FAVOR (supplied by Stockhausen of Greensboro, N.C.), and NORSOCRYL (supplied by Atochem). The superabsorbent particles come in a variety of sizes and morphologies, for example IM 1000 and IM 1000F. The 1000F is finer and will pass through a 200 mesh screen whereas IM 1000 has particles that will not pass through a 60 mesh screen. Another type of superabsorbent particle is IM 5600 (agglomerated fines). Superabsorbent particulate hydrophilic polymers are also described in detail in U.S. Pat. No. 4,102,340, which is incorporated herein by reference. That incorporated patent discloses hydrocolloid absorbent materials such as cross-linked polyacrylamides.

Other Particles

Many particles that form hydrogen bonds or coordinate covalent bonds are suitable for use with the present invention. Some such particles are listed in Table 1 with an indication of the function of the listed particles.

TABLE I

Particulates For Binding

| Name | Function |
| --- | --- |
| Aluminum Trihydrate | Fire retardant, astringent |
| Acediasulfone | Antibacterial |
| Agaricic acid | Antiperspirant |
| Alclometastone | Topical anti-inflammatory |

TABLE I-continued

Particulates For Binding

| Name | Function |
| --- | --- |
| Calcium alginate | Topical hemostatic |
| Amidomycin | Fungicide |
| Antimony oxide | Fire retardant |
| Apigenin | Yellow dye, mordant |
| Arsenic disulfide | Red Pigment |
| Aspirin | Anti-inflammatory; antipyretic |
| Azanidazole | Antiprotozoal (Trichomonas) |
| Azelaic acid | Antiacme |
| Baicalein | Astringent |
| Bendazac | Anti-inflammatory |
| Benomyl | Fungicide; ascaricide |
| Benzestrol | Estrogen |
| Benzylpenicillinic acid | Antibacterial |
| Benzylsulfamide | Antibacterial |
| Bergaptene | Antipsoriatic |
| Betasine | Iodine source |
| Bezitramide | Narcotic analgesic |
| Bibrocathol | Topical antiseptic |
| Bietanautine | Antihistaminic |
| Bifenox | Herbicide |
| Bifonazole | Antifungal |
| Binapacryl | Fungicide, miticide |
| Bis(p-chlorophenoxy) methane | Miticide |
| Bismuth aluminate | Antacid |
| Bismuth iodide oxide | Anti-infective |
| Bismuth phosphate | Antacid; protectant |
| Bismuth subcarbonate | Topical protectant |
| Bismuth subgallate | Astringent, antacid; protectant |
| Bisphenol A | Fungicide |
| Bitertanol | Agricultural fungicide |
| Bithionol | Topical anti-infective |
| Bromacil | Herbicide |
| Bromadiolone | Rodenticide |
| Bromcresol green | Indicator |
| Bromcresol purple | Indicator |
| Bromethalin | Rodenticide |
| p-Bromoacetanilide | Analgesic; antipyretic |
| 3-Bromo-d-camphor | Topical counterirritant |
| Bromophos | Insecticide |
| Bromopropylate | Acaricide |
| 5-Bromosalicyl-hydroxamic acid | antibacterial (tuberculostatic) |
| 5-Bromosalycilic acid acetate | Analgesic |
| Bromosaligenin | Anti-inflammatory |
| Bromthymol blue | Indicator |
| Broxyquinoline | Antiseptic; disinfectant |
| Bucetin | Analgesic |
| Bumadizon | Analgesic; anti-inflammatory; antipyretic |
| Bupirimate | Fungicide |
| Busulfan | Carcinogen, insect sterilant, antineoplastic |
| Butamben | Topical anesthetic |
| Butrylin | Insecticide |
| Butylated hydroxy-anisole | Antioxidant (BHA) |
| Butyl paraben | Pharmaceutic aid; food preservative |
| 4-tert-Butylphenyl salicylate | Light absorber |
| Cacotheline | Indicator |
| Cactinomycin | Antineoplastic |
| Cadmium salycilate | Antiseptic |
| Calamine | Skin protectant |
| Calcium carbonate | Antacid |
| Calcium saccharate | Pharmaceutic aid |
| Calcium tartrate | Preservative; deodorant; antacid |
| Cambendazole | Anthelminthic |
| Candicidin | Topical antifungal |
| Candidin | Topical antifungal |
| Capsaicin | Topical analgesic |
| Captan | Fungicide; bacteriostat |

TABLE I-continued

Particulates For Binding

| Name | Function |
|---|---|
| Carbadox | Antimicrobial |
| Carbamazepine | Anticonvulsant; analgesic |
| Carbarsone | Antiamebic |
| Carbaryl | Contact insecticide |
| Carbazochrome salycilate | Antihemorrhagic |
| Carbendazim | Fungicide |
| Carbochloral | Hypnotic |
| Carbophenothion | Miticide; insecticide |
| Carboquone | Antineoplastic |
| Carisoprodol | Skeletal muscle relaxant |
| Carthamin | Dye |
| Carvacrol | Disinfectant |
| Cephalin | Local hemostatic |
| Chalcomycin | Antibiotic |
| Chartreusin | Antibiotic |
| Chitin | Vulnerary |
| Chloramben | Herbicide |
| Chloramphenacol palmitate | Antimicrobial |
| Chloranil | Fungicide |
| Chlorbetamide | Antiamebic |
| Chlordimeform | Insecticide |
| Chlorfenac | Herbicide |
| Chlorfenethol | Acaricide |
| Chlorhexidine | Topical antibacterial |
| Chloroazodin | Antibacterial; topical anesthetic |
| Chlorophacinone | Anticoagulant rodenticide |
| p-Chlorophenol | Antiseptic |
| Chlorothricin | Antibiotic |
| Chlorotrianisene | Estrogen |
| Chloroxylenol | Antiseptic; germicide |
| Chlorphenesin | Topical antifungal |
| Chlorphenesin carbamate | Relaxant (skeletal muscle) |
| Chlorphenoxamide | Antiamebic |
| Chlorpropamide | Antidiabetic |
| Chlorpyrifos | Insecticide |
| Chlorquinaldol | Topical antibacterial |
| Chlorsulfuron | Herbicide |
| Chlorothion | Insecticide |
| Chlozoxazone | Relaxant |
| Cholesterol | Pharmaceutic aid |
| Chromic carbonate | Pigment |
| Chromic hydroxide | Pigment |
| Chromic oxide | Abrasive |
| Chromic phosphate | Green pigment |
| Chrysamminic acid | Explosive |
| Chrysarobin | Antipsoriatic |
| Cilastazol | Antithrombotic |
| Cinoxate | Sunscreen agent |

Other suitable particles include proteins, vitamins, zeolites and silica, which contain oxygen or nitrogen groups, or both. An example of a suitable zeolite is Abscents odor absorber available from UOP of Tarrytown, N.Y. An example of a suitable antimicrobial particle is chlorhexidine (N,N"-Bis(4-chlorophenyl)-3,12-diimino- 2,4,11,13-tetraazatetradecane-diimidamide). The list in Table I is by no means exhaustive as it can be readily determined for each type of particle whether it is capable of forming a hydrogen bond or a coordinate covalent bond. Many of the particles are non-absorbent, or not superabsorbent polymers.

The particles listed in Table 1 have chemical properties that make them suitable for binding to fibers with the binders of the present invention. The listed particles are organic or inorganic compounds that have little or no water solubility, yet have the capacity to hydrogen bond. Water solubility is preferably low, for example, less than 10 g dissolves completely in 300 ml of water at 25° C., more preferably less than about 1 g in 300 ml at 25° C. This low solubility allows the particles to remain solid, and the hydrogen bonding capacity allows them to adhere to the fibers. Once bound, the particles substantially retain a discrete particulate form instead of dissolving or fusing. More of the particles are discrete than fused.

The amount of binder added to the fibers can vary widely, for example from 0.05 to 80 percent of the total weight of the fibrous material, binders and particles. Antimicrobials such as chlorhexidine are effective in very low amounts, such as 0.05 percent. Superabsorbent particles are preferably added in an amount of 3–40 percent, especially 15–25 percent by weight.

Binder Characteristics

The particles are bound to the fibers by a water soluble polymeric binder selected from a predetermined group of binders that each have a hydrogen bonding functionality or coordinate covalent bond forming functionality on each repeating unit of the polymer. In accordance with the present invention, the predetermined groups of polymeric binders includes the set of binders consisting of polypropylene glycol (PPG); a PPG/PEG copolymer; polyacrylic acid; poly(caprolactone) diol; a polyamide such as polyglycine or another polypeptide; or a polyamine such as polyethyleneimine or polyvinyl pyridine. As used herein, a polymer is a macromolecule formed by chemical union of 5 or more identical combining units (monomers). A polyamine is a polymer that contains amine functional groups and a polyamide is a polymer that contains amide functional groups. Each of the binders has a hydrogen bonding or a coordinate covalent bonding functionality on each repeating unit (monomer) of the polymer. This repeating functionality may be a hydroxyl, carboxylic acid, amide, ether or amine. These binders are capable of forming hydrogen bonds because they have a functional group that contains an oxygen or a nitrogen.

The polyglycol has repeating ether units with hydroxyl groups at the terminal ends of the molecule, and polyacrylic acid has a repeating carboxyl group in which a hydrogen is bound to an electronegative oxygen, creating a dipole that leaves the hydrogen partially positively charged. The polyamide (such as a polypeptide) or polyamine has a repeating NR group in which a hydrogen may be bound to an electronegative nitrogen that also leaves the hydrogen partially positively charged. The hydrogen in both cases can then interact with an oxygen or nitrogen on the particle or fiber to form a hydrogen bond that adheres the binder to the particle and fiber. The electronegative oxygen or nitrogen of the binder can also form a hydrogen bond with hydrogens on the particle or fiber that have positive dipoles induced by oxygens or nitrogens to which the hydrogen is attached. The polyamide also has a carboxyl group with an electronegative oxygen that can interact with hydrogen atoms in the particles or fibers.

Thus, the binders enhance the hydrogen bonding (a) between the fibers and binder; and (b) in the case of particles with hydrogen bonding functionalities, between the binder and the particles.

Alternatively, the binder may form a coordinate covalent bond with the particles and a hydrogen bond to the fibers. For example, the oxygen or nitrogen on the binder has an unbound pair of electrons that can be donated to an empty orbital in the particle to form a coordinate covalent bond. For example, one free pair of electrons on the oxygen or nitrogen can be donated to the empty p orbital of a boron containing particle to form a coordinate covalent bond that adheres the particle to the binder. The fibers themselves contain functional groups that can form hydrogen bonds with the binder, and allow the binder to adhere to the fiber. Cellulosic and synthetic fibers, for example, contain hydroxyl, carboxyl, amide, ether and ester groups that will hydrogen bond with the hydroxyl, carboxylic acid, amide or amine groups of the binder. Non-cellulosic or non-synthetic fibers that have these functionalities can also be used, for example silk which has an amide linkage. Hence the binder will adhere the particle with a coordinate covalent bond and the fiber will adhere with a hydrogen bond.

In some preferred embodiments, the binder is bound to both the fibers and the particle by hydrogen bonds. A polypropylene glycol binder, for example, can be used to bind polyacrylate hydrogel particles to cellulosic fibers. The hydroxyl and ether groups on the glycol binder participate in hydrogen bonding interactions with the hydroxyl groups on the cellulose fibers and the carboxyl groups on the polyacrylate hydrogel, as shown below:

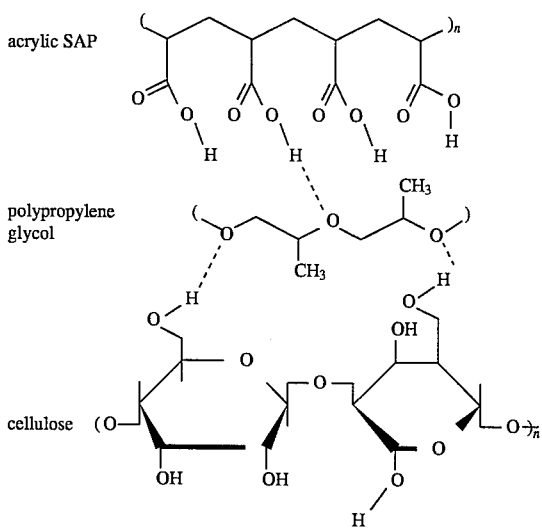

Hence the binder will adhere both the particle and fiber with hydrogen bonds. The presence of a hydrogen bonding functionality on each repeating unit of the polymeric binder has been found to increase the number of hydrogen bonding interactions per unit mass of polymer, which provides superior binding efficiency and diminishes separation of particles from the fibers. The repeating ether functionality on the glycol binder provides this efficiency in the example diagrammed above. A repeating carboxyl group is the repeating functionality on polyacrylic acid, while repeating carbonyls and NR groups (wherein R is either an H or alkyl, preferably lower alkyl, i.e. less than five carbons, in the normal or iso configuration) of the amide linkages are the repeating functionalities on polyamides such as polypeptides. A repeating amine group is present on polyamines.

The polymeric organic binders of the present invention have been found to increase in binding efficiency as the length of the polymer increases, at least within the ranges of molecular weights that are reported in the examples below. This increase in binding efficiency is attributable to the increased number of hydrogen bonding or coordinate covalent bonding groups on the polymer with increasing molecular length. Each of the polymeric binders has a hydrogen bonding or coordinate covalent bonding functionality on each repeating unit of the polymer, hence longer polymers provide more hydrogen bonding groups or coordinate covalent bonding groups that can participate in hydrogen bonding interactions or coordinate covalent bonds.

Although the invention is not limited to binders of particular molecular weights, polymeric binders having a molecular weight greater than 500 grams/mole are preferred because they provide attractive physical properties, and the solid is less volatile and more thermoplastic as compared to small polymeric binders. Binders with molecular weights greater than 4000 grams/mole are especially preferred, because they have minimal volatility and are less likely to evaporate from the fibers. In some particular embodiments, polymers with molecular weights between 4000 and 8000 grams/mole have been used. Polymers with molecular weights above 8000 may be used, but exceedingly high molecular weight polymers may decrease binding efficiency because of processing difficulties.

Certain binders have greater binding efficiency because their repeating functionality is a more efficient hydrogen bonding group. It has been found that repeating amide groups are more efficient than repeating carboxyl functionalities, which are more efficient than repeating hydroxyl functionalities, which in turn are more efficient than amine or ether functionalities. Hence, binders may be preferred that have repeating amine or ether functionalities, more preferably repeating hydroxyl functionalities, and even more preferably repeating carbonyl or carboxyl functionalities, and most preferably repeating amide functionalities. Binding may occur at any pH, but is suitably performed at a neutral pH of 5–8, preferably 6–8, to diminish acid hydrolysis of the resulting fibrous product.

The moisture content of the fibers during the binding reaction is 0.5–50%, suitably 5–40%, or preferably 5–20% water by weight of the fibers, binder and particle. A moisture content greater than 20%, more preferably 30%, or in the range 20–50%, or 30–50%, can be used even though such high moisture contents would interefere with intermediate anhydride formation and inhibit formation of covalent bonds (e.g. ester bonds) in the production of high bulk fibers. Particles may be added to the fibers such that the particles are distributed throughout a fibrous product without being confined to a surface of the product. The particles can be distributed throughout the depth of a fiber product such as a mat or web.

The binder is suitably present in the treated product in an amount of at least 3 percent and no more than 80 percent by weight of the fibers, particles, and binder ("percent by weight"). In especially preferred embodiments, the binder is present in an amount of 5–30 percent by weight. Below about 3 percent, an insufficient amount of binder is present to achieve adequate binding, while using excessive amounts of binder can introduce unnecessary expense into the binding process. High percentages of binder can also cause processing problems because the binder material transfers to equipment surfaces.

The binders of the present invention also provide numerous process advantages. Binding of particles to the fibers can occur, for example, without external application of heat. Hence particle binding may occur at ambient temperature if desired. The present invention is therefore distinct from prior art crosslinking processes in which elevated temperatures are required to covalently crosslink cellulose groups to each other.

Thermoplastic binders may also be used to help bind fibers to each other and particles to fibers. The binder that has the hydrogen bonding or coordinate covalent bonding functionalities may itself be thermoplastic. The polymeric binders of the present invention have the advantage of being thermoplastic solids. Hence fibers treated in accordance with the present invention can be thermobonded by elevating the fiber temperature above the melting temperature of the binder to melt the thermoplastic binder and thermoplastically bind the fibers to each other and the fibers to the particles. Alternatively, an auxiliary or second binder can be applied to the fibers as a solid at room temperature, and the temperature of the second binder elevated above its melting point to thermobond the fibers and particles. The auxiliary binder may be applied to the fibers either before or after the primary binder is applied, but before thermobonding.

The binders of the present invention may be used with fibers that have substantial intrafiber covalent crosslinks (such as HBA available from Weyerhaeuser) or fibers which are substantially free of infrafiber covalent crosslinking. Examples of individualized intrafiber crosslinked fibers are seen in European Patent Applications 440 472 A1 and 427 317 A2, which produce products that those publications describe as being substantially free of interfiber bonds. The fibers of the present invention do not need to be processed as in those European applications to eliminate interfiber bonds. Binders of the present invention can therefore be used with natural fibers that have substantial interfiber bonding, which is defined as fibers that have not been processed as in European Applications 440 472 A1 and 427 317 A2 to substantially eliminate interfiber bonds. Cellulose fibers that have not been so processed are substantially free of intrafiber bonds.

Fibers that have high bulk from intrafiber covalent crosslinks are prepared by individualizing the fibers and curing them at an elevated temperature (above 150° C.). Initial application of the binder on such high bulk fibers preferably occurs after the curing step, particularly if the binder is capable of functioning as a crosslinking material. A binder that can also crosslink is a polycarboxylic acid. If this binder is present during curing, the binder will be consumed during the curing step to form covalently crosslinked ester bonds. When this occurs, the binder is no longer available for hydrogen bonding or coordinate covalent bonding, and particle binding to fibers is ineffective.

In some circumstances the binder can be applied before curing, even if the binder is also a crosslinking material. Such a binder can be present if steps are taken to inhibit formation of anhydride intermediates that are required for covalent ester bond formation. Anhydride formation can be inhibited, for example, by adding a sufficient amount of water to the fibers to inhibit anhydride formation without preventing all covalent crosslinking from occurring. Inhibition of anhydride formation can occur when the fibers have 30% water by weight and are cured at 150° C. for 20 minutes. Hence, at least 30% water by weight should be present, or 30–50% water. Higher amounts of water within this range are preferred when curing at temperatures higher than 150° C., or for periods longer than 20 minutes.

In accordance with this invention, the binders may be applied to fibers before, subsequent, or simultaneously with addition of the particles. Simultaneous addition can be accomplished by two separate streams of particles and binder that are simultaneously directed at a fibrous substrate, or alternatively merged immediately prior to impacting against the substrate.

The binders of the present invention have the advantage of being activatable or reactivatable by addition of water or by heating. Hence, a liquid binder can be applied to cellulose fibers, loose or in another form, such as a cellulose mat, in the absence of the particles to be bound. The binder is then dried or allowed to dry, for example until the binder and fiber reach an equilibrium moisture content with ambient air. Alternatively, the binder can be applied as a solid, for example, sprinkled onto a fiber mat. At a later stage of processing, a liquid such as water is added to the fibers resulting in an activation of the binder. The particulates may then be added, and the binder secures the particulates to the fibers. This subsequent processing of the fibers can occur, for example, at a separate plant from the fiber production location. Therefore, manufacturers of products can add particulates of interest to their manufacturing applications (e.g., superabsorbent particles or fibers; antimicrobial particles, etc.) at the place of manufacture of the products. Also, more than one type of particulate material may be added, if desired.

Activation (which includes reactivation) can be of all the fibers, or only portions of the fibers, such as target zones or portions of the mat where particulate binding is desired. The particles may then be added to the mat and adhered to the target zones of the mat which have been moistened. In other embodiments, the binder is applied as a solid and heated (for example in a specific target zone) during a later processing stage to activate the binder by softening it such that it binds the particles to the fibers.

In yet other embodiments, the binder is applied to the fibers and then activated by applying kinetic energy to the fibers. Neat polypropylene glycol (MW 3000) binder, for example, may be sprayed on fibers and allowed to air dry. Desired particles are then added to the fibers as they are mechanically agitated in a blender or defiberizer to kinetically activate the binder and bind the particles to the fibers.

Suitable binders may be selected from the group consisting of polypropylene glycol and copolymers thereof; polypropylene glycol and polyacrylic acid; polypropylene glycol, polyacrylic acid, and a polyamide; polypropylene glycol, polyacrylic acid, a polyamide and a polyamine; polyacrylic acid alone; polyacrylic acid and a polyamide; polyacrylic acid, a polyamide and a polyamine; a polyamide alone; a polyamide and a polyamine; or a polyamine alone. Poly(caprolactone) diol may optionally be included in any of these groups.

The group consisting of polyacrylic acid, polyamide and polyamine has been found to have a especially good binding efficiency. Among polyamides, polypeptides are especially preferred.

Binding is performed under conditions that favor formation of hydrogen bonds or coordinate covalent bonds, and discourage formation of covalent bonds. Conditions that favor covalent bonds are those disclosed in U.S. Pat. Nos. 4,412,036 and 4,467,012 wherein particle and binder would be laminated between tissue layers under high temperature and pressure to form laminated adherent tissue layers. That patent teaches that minimal adhesion occurs at 200 pli (pounds per linear inch, as in a calendar press) if no external heat is supplied, but adhesion improves as the reaction temperature increases. Improved adhesion of the tissue layers occurs because of enhanced covalent bonding as the temperature increases. The present invention, in contrast, produces a product under conditions that favor formation of hydrogen or coordinate covalent bonds. Hence, the particles can be bound to the fibers in the absence of the external application of heat or pressure. Particles may also be bound and the resulting fiber product densified, for example at less than 200 pli (pounds per linear inch, as in a calendar press) or 8000 psi, or less than 100 pli (4000 psi), in the absence of external application of heat to produce a product in which a substantial portion of the particles are bound by non-covalent bonds (hydrogen or coordinate covalent bonds). A substantial portion of particles bound by non-covalent bonds means at least half of the bonds binding the particles are other than covalent bonds, for example by hydrogen or coordinate covalent bonds.

In yet other examples, particles may be bound in the absence of external application of pressure, but at elevated temperatures.

In particularly preferred embodiments, the particles are substantially entirely bound to the fibers non-covalently.

Binding Examples

Several examples are given below illustrating use of the polymeric binders of the present invention to attach superabsorbent particles to southern bleached kraft pulp.

EXAMPLE I

A 321 gram amount of NB-416 southern bleached kraft fluff obtained from Weyerhaeuser Company may be air-entrained in a blender-like mixing device and 100 grams of poly(caprolactone) diol (average molecular weight 2000, supplied by Aldrich Chemical Company of Milwaukee, Wis.) dissolved in 100 ml of deionized water may be sprayed onto the fluff as a binder. Then 435 grams of starch graft polyacrylate hydrogel fines (IM 1000F; supplied by Hoechst-Celanese of Portsmouth, Va.) may be added and mixed. The product may then be removed from the blender, and spread out in a fume hood to air dry overnight. The resulting product may then be airlaid on a small airlay line, from M & J Machines (of Horsens, Denmark) and thermobonded at 140° C. for one minute to produce a web containing 40% superabsorbent particles (SAP) attached to the individualized fibers. This binder has a low melting point, hence raising the temperature to 140° C. melts the binder and allows it to flow over the fibers and particles to enhance hydrogen bonding interactions and provide mechanical encapsulation that further binds the fibers and particles. A polypropylene glycol/polyethylene glycol binder would also behave in this manner.

EXAMPLE II

A 321 gram amount of southern kraft fluff was air-entrained in a blender-like mixing device and 154 grams of a 65% solution of polyacrylic acid (average molecular weight=2,000; supplied by Aldrich Chemical Company of Milwaukee, Wis.) diluted with 100 ml of deionized water was sprayed onto the fluff. Then 435 grams of polyacrylate hydrogel (FAVOR 800 supplied by Stockhausen of Greensboro, N.C.) was added into the mixing device and mixed with the fluff and polyacrylic acid binder. The product was removed and spread out to dry and then fed to a hammermill with a three-eighths inch round hole screen and shunted to a small airlay line to produce a web containing 40% SAP attached to the individualized fibers.

EXAMPLE III

A 321 gram amount of southern bleached kraft fluff is air-entrained in a blender-like mixing device and 100 grams of polyglycine (molecular weight=5,000–15,000; supplied as a dry powder by Sigma Chemical Company of St. Louis, Mis.) diluted with 100 ml of deionized water is sprayed onto the fluff. Then 435 grams of starch graft polyacrylate hydrogel fines (IM 1000F; supplied by Hoechst-Celanese of Portsmouth, Va.) is added and mixed. The product is removed and spread out in a fume hood to dry overnight. The resulting product is fed into a Fitz hammermill with a three-eighths inch round hole screen and shunted to a small M & J airlay line to produce a web containing 40% SAP attached to the fibers.

EXAMPLE IV

A 321 gram amount of southern bleached kraft fluff is air-entrained in a blender-like mixing device and 200 grams of a 50% solution of polyethyleneimine (molecular weight= 50,000–100,000; supplied by ICN Biomedicals, Inc. of Costa Mesa, Calif.), or polyvinyl pyridine is then sprayed on the fluff. Then a 435 gram amount of starch graft polyacrylate hydrogel fines (IM 1000F; supplied by Hoechst-Celanese of Portsmouth, Va.) is added and mixed. The product is removed and spread out in a fume hood to dry overnight. The resulting product is fed into a Fitz hammermill with a three-eighths inch round hole screen and shunted to a small M & J airlay line to produce a web containing 40% SAP attached to the fibers.

The classes of binders that encompass those described in Examples I–IV are especially preferred over other multiple hydrogen bonding functionality polymers for a number of reasons. One important reason is that their functionalities produce very strong, effective hydrogen bonding. Other important reasons include their relative lack of reactivity (as compared with polyaldehydes or polyisocyanates) and their low toxicity (again, as compared with polyaldehydes or polyisocyanates).

EXAMPLE V

As previously described, repetition of a hydrogen bonding group on each repeating unit of a polymer has been found to produce a binder that provides superior binding of particles to fibers, as compared to polymeric binders in which the hydrogen bonding functionality is not present on all the repeating units. This example shows the difference in binding efficiency between a 20% carboxylated polymer and a 100% carboxylated polymer. A bound sample was prepared as in Example I using a 20% carboxylated ethylene acrylic acid copolymer and a 100% carboxylated PAA. A sample of each was subjected to the same mechanical agitation (to simulate machine processing required to make a web), screened through a descending series of sieves to remove unattached SAP, and subjected to an absorbent capacity test (less attached SAP would result in a lower absorbent capacity). The result of the test was measured by weighing the unabsorbed liquid (0.9% saline) from a standardized insult, hence a lower number indicates more liquid absorbed or higher absorbent capacity.

A sample of the 20% carboxylated polymer (15% of the total mix) gave a beaker test result of 19.5 grams. A similar sample of polypropylene glycol would give a result of about 20.0 grams. However, the hydrogen bonding functionality of PPG is not as efficient as the carboxyl functionality of PAA. A similar sample of polyacrylic acid (100% carboxyl functionality of PAA) gave a result of 11.3 grams. A comparison of the 20% and 100% carboxylated polymers shows a substantial increase in SAP binding efficiency, as measured by an increase in absorbency of the product.

Binder Activation Examples

Binder reactivation in the present invention allows binder to be added to fibers either before or after particles are added to the fibers. The binder is subsequently activated by addition of liquid, heat, or agitation, and particles are bound to the fibers. The particles may be added to the fibers either before binder activation, after binder activation, or simultaneous with activation. If SAP is to be added to cellulose fibers, for example, the binder may be applied to a pulp sheet which is subsequently fiberized. A liquid such as water may be added to the pulp before or after fiberization, and SAP may be added before or after water addition, or simultaneously with the water. If SAP is added after water addition, the SAP should be applied to the fibers prior to complete evaporation of the added water from the fibers.

Alternatively, the binder may be activated by heat. A solid binder may be applied to a pulp sheet before fiberization or mixed with fiberized pulp after fiberization. A liquid binder may alternatively be applied and allowed to dry. The solid or dried binder is then activated by heating it above its softening temperature. SAP may be added before, after, or simultaneously with heat addition. If SAP is added after heat activation, the SAP should be applied to the fibers prior to resolidification of the binder.

The following example will illustrate several specific applications of the activation process, and are not intended to limit the invention to the disclosed methods.

EXAMPLE VI

The method of Example I above could be modified such that the SAP is not added until after the web is heated to 140° C. A solid polyethylene glycol/polypropylene glycol copolymer could be substituted for the binder of Example I, and it would melt well below 140° C., and in its liquid form bind the SAP to the fibers. The SAP could be applied randomly across the heated product, or applied specifically to a targeted zone of the product where enhanced absorbency is specifically desired.

EXAMPLE VII

A southern kraft pulp sheet would be immersed or sprayed with 154 grams of a 65% solution of polyacrylic acid diluted with 100 ml of deionized water. The sheet is then allowed to air dry overnight, heated in an oven at 80° C. for thirty minutes and conditioned in a 50% relative humidity chamber overnight. The sheet is then misted with water to raise its moisture content to 17–20% as it is fed into a Fitz hammermill filled with a three-eighths inch hole screen. Polyacrylate hydrogel particles of FAVOR 800 supplied by Stockhausen would simultaneously be added to the mill by a screw feed device, mixed with the fluff, shunted to an M & J airlay forming machine and airlaid to form a web containing bound SAP throughout the web, i.e., without being confined to a surface of the web. Mixing SAP throughout the fluff helps produce a product in which SAP is homogeneously or randomly distributed, which diminishes problems of gel blocking.

EXAMPLE VIII 900 grams of KittyHawk pulp sheet (from the Weyerhaeuser Co., containing 22% synthetic fiber) is immersed in a 10% by weight solution of polyglycine for thirty minutes. The 5 inch wide sheet was then uncoiled on a lab bench to air dry overnight, heated in an oven at 80° C. for thirty minutes and conditioned in a 50% relative humidity chamber overnight. The sheet is fed into a Fitz hammermill fitted with a three-eighths inch hold screen, defiberized, shunted to an M & J airlay line, and airlaid into a web. As the web emerges, circular target zones of the web are misted with water from a spray bottle to raise the moisture content to 17–21% in the target zone. Five gram aliquots of starch graft polyacrylate hydrogel fines (IM 1000F; supplied by Hoechst-Celanese of Portsmouth, Va.) are subsequently sifted onto the target zones to yield a web with SAP bound in target zones. The SAP does not form a confluent layer, but is instead present in particulate form on and below the surface of the web.

EXAMPLE IX

A 900 gram amount of southern bleached kraft fluff pulp sheet is sprayed with a 50% solution of polyglycine so that the moisture content is 17–21% as the sheet is fed into a Fitz hammermill fitted with a three-eighths inch hole screen. Starch graft polyacrylate hydrogel fines (IM 10000F; supplied by Hoechst-Celanese of Portsmouth, Va.) are simultaneously added to the mill by a screw feed device as the sheet is fed into the hammermill, mixed with the fluff, shunted to an M & J airlay forming machine and airlaid to form a web. The fines are intimately mixed with the fluff in the fibermill and bound to the fibers by the polyglycine binder to produce a web with particles distributed throughout its width, and not restricted to a superficial surface.

Thermoplastic Binders

In yet another aspect of the invention, a second binder can be added to the fibers (either before or after a first binder) to help bind the fibers to each other, and provide additional binding between the fibers and particles. A suitable second binder would be a thermoplastic or thermosetting binder. In the case of thermoplastic polymers, the polymers may be a material which remains permanently thermoplastic. Alternatively, such polymers may be a material which is partially or fully crosslinkable, with or without an external catalyst, into a thermosetting type polymer. As a few specific examples, suitable thermoplastic binders can be made of the following materials ethylene vinyl alcohol
polyvinyl acetate
acrylic
polyvinyl acetate acrylate
acrylates
polyvinyl dichloride
ethylene vinyl acetate
ethylene vinyl chloride
polyvinyl chloride
styrene
styrene acrylate
styrene/butadiene
styrene/acrylonitrile
butadiene/acrylonitrile
acrylonitrile/butadiene/styrene
ethylene acrylic acid
polyethylene
urethanes
polycarbonate
polyphenylene oxide
polypropylene
polyesters
polyimides In addition, a few specific examples of thermoset binders include those made of the following materials:

epoxy
phenolic
bismaleimide
polyimide
melamine/formaldehyde
polyester
urethanes
urea
urea/formaldehyde More than one of these materials may be used to treat the fibers. For example, a first coating or sheath of a thermoset material may be used followed by a second coating of a thermoplastic material. The superabsorbent particles or other particles are then typically adhered to the outer binder material. During subsequent use of the fibers to make products, the thermoplastic material may be heated to its softening or tack temperature without raising the thermoset material to its curing temperature. The remaining thermoset material permits subsequent heating of the fibers to cure the thermoset material material may be cured at the same time the thermoplastic material is heated by heating the fibers to the curing temperature of the thermoset with the thermoplastic material also being heated to its tack temperature.

Certain types of binders enhance the fire resistance of the treated fibers, and thereby products made from these fibers. For example, polyvinyl chloride, polyvinyl dichloride, ethylene vinyl chloride and phenolic are fire retardant.

Surfactants may also be included in the liquid binder as desired. Other materials may also be mixed with the liquid binder to impart desired characteristics to the treated fibers. For example, particulate material, such as pigments, may also be included in the binder for application to the fibers.

EXAMPLE X

As previously described, an auxiliary binder can be used in addition to the polymeric binders of the present invention. A 3210 gram amount of southern bleached kraft binder (NB-416, supplied by Weyerhaeuser Company) is air entrained in a blenderlike mixing device and sprayed with 2128 grams of a polyvinyl acetate latex (PN-3666H, supplied by H. B. Fuller of Minneapolis, Minn.). While still mixing, 4073 grams of a water swellable polyacrylate hydrogel (IM 1000-60, supplied by Hoechst-Celanese of Portsmouth, Va.) is added and the resulting mixture is then sprayed with 1160 grams of a 50% solution of polypropylene glycol (supplied by Union Carbide of Danbury, Conn.). The blender is then stopped and the mixture was shunted into a flash tube dryer. The dried product is then airlaid as a 16 inch wide web on a Danweb airlay machine, pressed to a density of approximately 0.15 g/cc, and thermobonded at 140° C. for thirty seconds. The resulting web would have 40% bound SAP and improved tensile strength (as compared to untreated fluff with SAP).

Application of Binder

The binders of the present invention can be added to the fibers in any convenient manner. One such procedure is to spray the binder or binders on a web of the fibers that is conveyed past a sprayer on a conveyor belt. Alternatively, loose fibers may be allowed to fall past a sprayer, or loose fibers may be moved on a conveyor belt past a sprayer. The loose fibers may also be slurried with or immersed in binder. For solid binders, blending of the fiber and binder may be accomplished or the binder may simply be sprinkled onto or otherwise comingled with the fibers. The fibers may also be sprayed or immersed in the binder, or binder particles may be applied thereto. These fibers can, while still wet in the case of a liquid binder or following reactivation of a liquid or solid, be combined with the particles. The fibers can also be allowed to dry for later reactivation with a reactivation liquid and combined with the particles at that time. Particles may be added from conventional volumetric feeders in a hammermill or from injectors on a paper making line.

One method for uniformly coating the fibers with a binder and adding the particles is shown in U.S. Pat. No. 5,064,689, which is incorporated herein by reference. However, the invention is not limited to any specific mechanism for combining the fiber, binder and particles.

Composite Absorbent Product

In accordance with the present invention, absorbent structures may be made from the fibers, with binder and particulates in accordance with the present invention. These articles may be composite structures (e.g., made of plural materials). For example, the articles may have a core of plural types of fibers, or fiber layers, with or without covering materials. These products are capable of absorbing significant quantities of water and other fluids, such as urine and body fluids. Such products include, but are not limited to, disposable diapers, sanitary napkins, incontinent pads, towels and the like.

Figure 2:
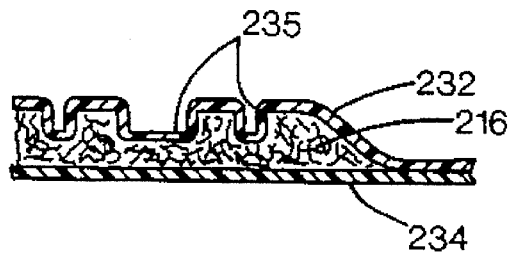
FIG. 2 represents a partial sectional view of the pad of FIG. 1.

As best shown in FIGS. 1 and 2, an absorbent towel 200 may have a core 216 with a cover sheet 232 and a backing sheet 234. The core 216 may be comprised of fibers with the binders of the present invention and particulate materials, such as superabsorbent particles secured to the fibers by the binder. The binder containing fibers may be blended with other fibers as well in the core. Cover sheet 232 is made of any suitable material, including liquid permeable, nonwoven materials, which will readily permit the passage of liquid through the cover sheet to the absorbent pad 216. The following list of liquid permeable materials is provided by way of example only: nonwoven sheets of polypropylene, rayon, nylon fibers, polyester fibers, and blends thereof. A specifically preferred cover sheet material for wipes is a 70% rayon/30% polyester blend having a basis weight of 21.5 grams/m$^2$, available from the Scott Paper Company.

The backing sheet 234 may be, but is not necessarily, made of a liquid impermeable material, including but not limited to, films of polyethylene, polypropylene and polyester and blends thereof along with nylon and polyvinyl chloride films. A specifically preferred backing sheet material is a polyethylene film from Dow Chemical Company.

Figure 3:
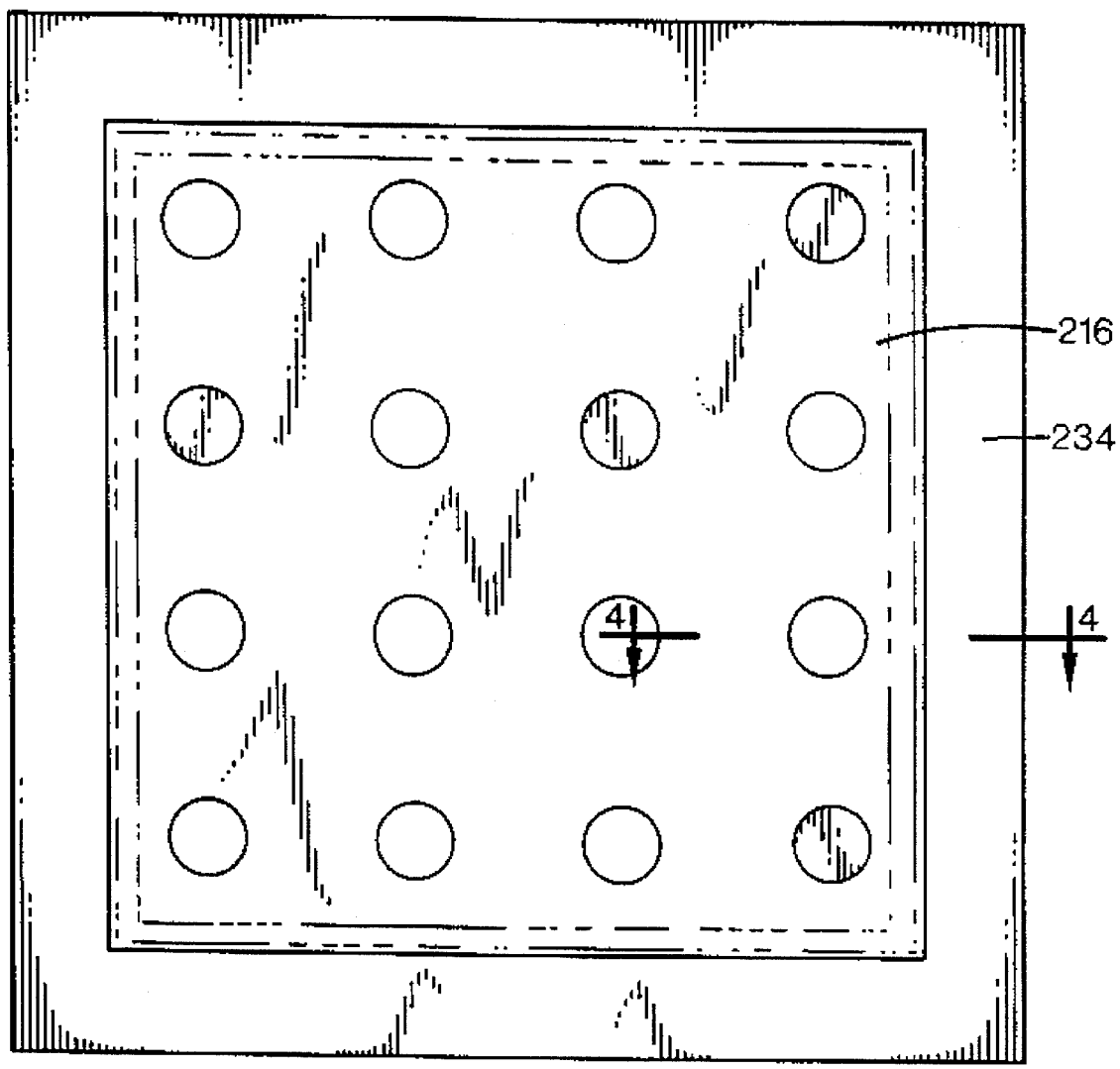
FIG. 3 represents a top plan view of an alternative pad structure formed in accordance with the present invention.
Figure 4:
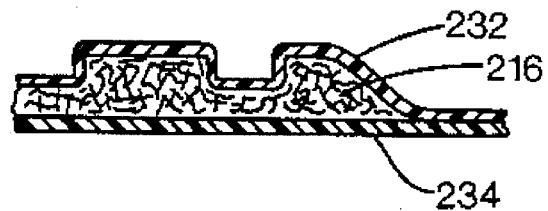
FIG. 4 represents a partial sectional view of the pad of FIG. 3, taken along line 4—4 of FIG. 3.

FIGS. 1–4 illustrate examples of different types of absorbent pad structures which may be formed from fibers of the present invention, whether or not they are blended with other fibers. FIGS. 1 and 2 represent an absorbent pad having a heat embossed screen pattern. FIGS. 3 and 4 represent an alternative absorbent pad having a dot matrix pattern. Pads having no pattern may also be used. A pad having a cover sheet and a backing sheet may be formed, for example, by placing a square fiber piece cut from the sheet onto a corresponding precut backing sheet. A corresponding precut cover sheet is placed over the top of the fiber on the backing sheet. This assembly may then be adhesively bonded.

Figure 5:
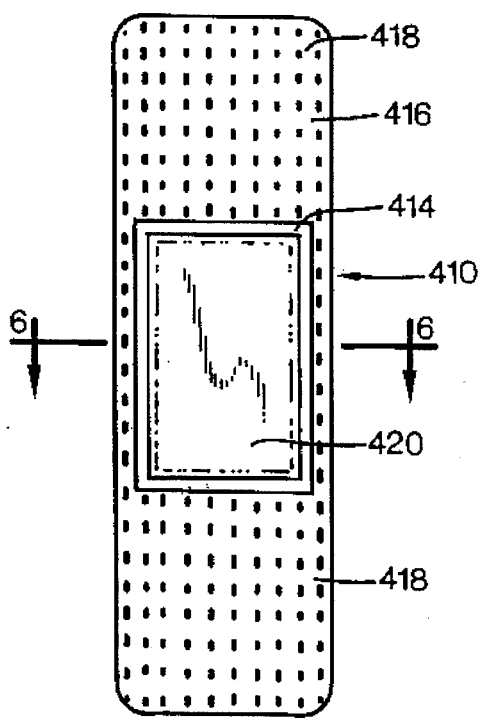
FIG. 5 illustrates a plan view of a bandage incorporating fibers of the present invention.
Figure 6:
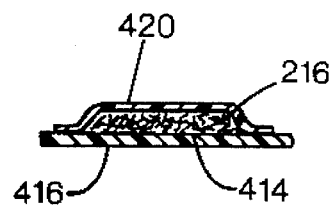
FIG. 6 is a sectional view of the bandage of FIG. 5, taken along line 6—6 of FIG. 5.

With reference to FIGS. 5–8, absorbent structures in the form of bandages or dressings are shown. In FIGS. 5 and 6, a bandage 410 for application to a wound to absorb blood and other bodily fluids is shown. An absorbent pad 216 (FIG. 6) is securely mounted to an exterior or pad mounting surface 414 of a backing strip 416. Any suitable mounting or securing means may be used to affix pad 216 to the surface 414 of the strip 416. However, it is preferable for surface 414 to be coated with an adhesive so that the pad 216 may be adhesively mounted in place. An exemplary adhesive is ethylene vinyl acetate adhesive. It is also desirable for the overall surface 418 of backing strip 416 to be coated with a conventional adhesive. Surface 418 is the surface which is affixed to the area of the skin surrounding the wound. Conventional "peel-back" tabs may be used to protect the adhesive coating and pad 216 until the bandage is to be applied. This type of backing strip is well known in the art.

The backing strip 416 may be of any known flexible material suitable for application to the skin. It is preferable for the strip 416 to be of a material which is impermeable to the passage of liquid so that fluid from a wound is contained by the bandage. However, the strip 416 may be apertured or otherwise breathable to permit air to reach the wound to promote the healing process. A specific example of a suitable backing strip 416 is a polyethylene film.

As in the other structures described, a variety of combinations of antimicrobials and other particles may be used in such a bandage. Again, however, the particles are adhered securely in place when the particles have a hydrogen bonding or a coordinate covalent bonding functionality, the fibers to which these particles are bound have a hydrogen bonding functionality, and wherein the binder is selected from the group consisting of a polypropylene glycol, a polypropylene glycol/polyethylene glycol copolymer, polyacrylic acid, a polyamide, or a polyamine and the polymeric binder has a hydrogen bonding or a coordinate covalent bond forming functionality on each repeating unit of the binder. Two different particles, such as antimicrobials in particulate form, may be adhered to the same fiber. In the alternative, each different type of antimicrobial particle or other particle may be adhered separately to different fibers. Also, blends of fibers may be included in absorbent structures such as pad 216. For example, these blends may include fibers with adhered antimicrobial (one or more antimicrobials) particles and adhered superabsorbent particles; fibers with one or more antimicrobial particles without superabsorbent particles blended with fibers having adhered superabsorbent particles with or without antimicrobial particles; and combinations of such fibers with untreated fibers and/or binder coated fibers without superabsorbent particles or antimicrobial particles. In addition, other particles, such as anticoagulants or hemostatics may be attached to the fibers.

The absorbent pad 216 of bandage 410 may also include a cover sheet 420. Cover sheet 420 is typically made of any suitable material which will readily permit the passage of liquid through the cover sheet to the absorbent pad 216, such as nonwoven fiber webs of fibers such as, for example, rayon, nylon, polyester, propylene and blends thereof. One specifically preferred cover sheet material is a 70 percent rayon/30 percent polyester blend having a basis weight of 18 g/m$^2$ from Scott Paper Company.

Figure 7:
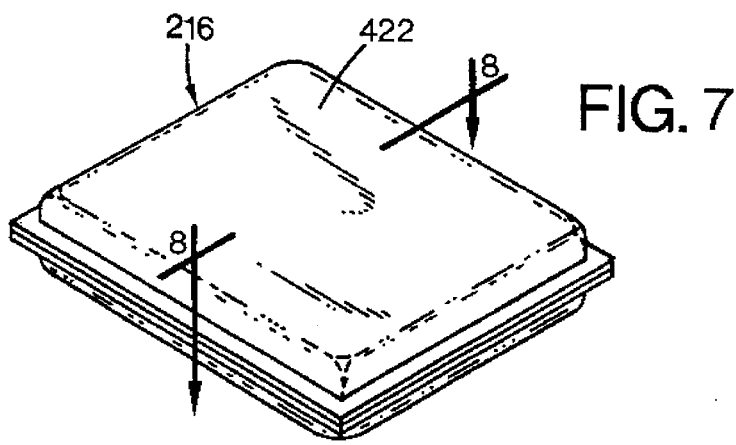
FIG. 7 is a perspective view of an absorbent structure of fibers of the present invention.
Figure 8:
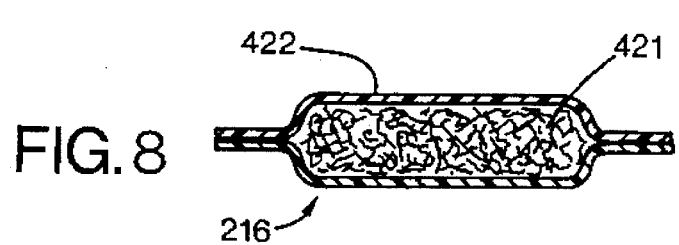
FIG. 8 is a cross-sectional view of the structure of FIG. 7, taken along line 8—8 of FIG. 7.

The dressing 216 shown in FIGS. 7 and 8 illustrates fibers 421 placed within an enclosure 422. Enclosure 422 has at least one liquid permeable surface through which fluid or liquid may pass to be absorbed by the fibers. The enclosure containing the loose fibers may be secured to the skin using adhesive tape, for example. Again, the fibers 421 preferably include antimicrobial particles attached to at least some of the fibers.

Figure 9:
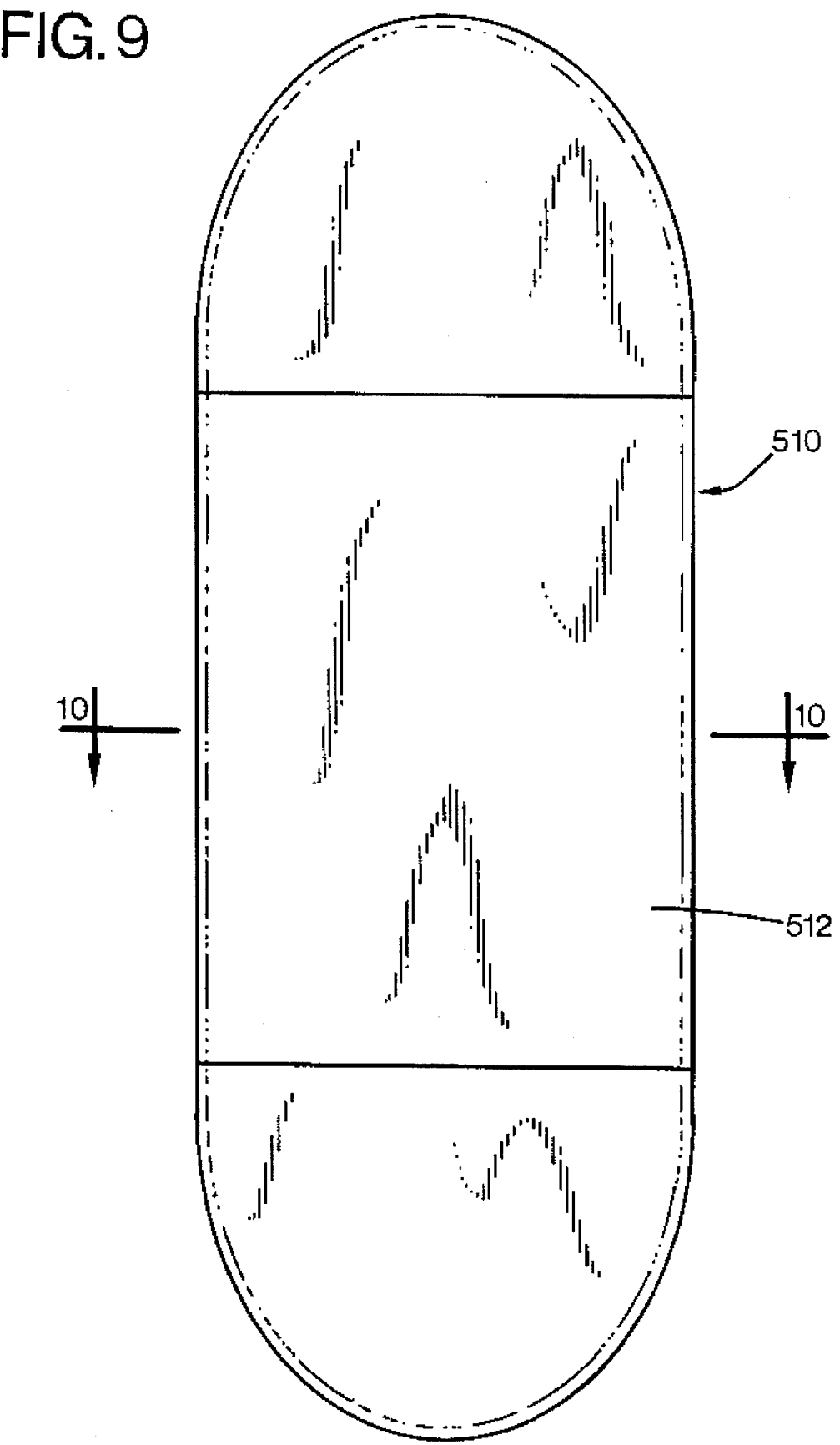
FIG. 9 is a plan view of a feminine hygiene appliance incorporating fibers of the present invention.

FIGS. 9 and 10 illustrate fibers of the present invention incorporated into a feminine hygiene appliance such as a feminine pad or tampon. In this case, the feminine pad 510 is illustrated as having a cover sheet 512. The loose fibers having adhered antimicrobial particles, which may alternatively be in the form of a pad, are included within the interior of the feminine appliance as indicated at 216 in FIGS. 2 and 4. The cover 512 is preferably liquid permeable so that bodily fluids may reach the interior of the pad for purposes of absorption. The cover 512 may be wrapped around the core 216 (as indicated by edges 514, 515). A backing sheet 516, preferably of a liquid impermeable material, may be adhered to the edges 514, 515 at the underside of the core. An adhesive containing strip, such as indicated at 520, which may have a peelable or removable cover, may be mounted to the backing sheet 516 for use in adhering the pad, for example to a user's undergarment, during use.

FIGS. 11 and 12 illustrate a conventional disposable diaper 550 with a core 552 which is comprised of fibers of the present invention with adhered superabsorbent particulate materials. These particulate materials may be confined to a target zone (for example, the front portion of a diaper indicated at 556) or of a heavier concentration in the target zone. This can be accomplished by airlaying fibers of the present invention in such a zone. Also, the core may be reactivated by melting the binder or moistening the target zone with water. The superabsorbent particles may be sprinkled on or otherwise applied to this wetted zone. As the zone dries, the particles are adhered in place.

Densification

The products such as described above, as well as webs of the fibers of the present invention, can also be densified by external application of pressure to the web. The web of Example 2, for instance, could be densified by passing it through a set of calendar rolls set at 60 and 90 pli respectively to yield sheets with increased densities. Densification may alternatively be provided by compaction rolls or presses. The present inventors have found that densification is facilitated in the products treated with the polymeric organic binders of the present invention. Either liquid or solid binders provide enhanced densification, but solid binders are most preferably moistened or otherwise fluidized to provide this benefit. Products that are treated with the binders of the present invention require less heat and pressure than untreated fibers to densify to a given density. Densification is preferably performed to produce a product that has a density of about 0.1 to 0.7 g/cc, more preferably 0.1 to 0.3 g/cc. Ease of densification is associated with the hydrogen bonding and coordinate covalent bonding of the particles to the fibers, and is particularly notable when at least 5%, and preferably 10% by weight of the fibers, particles and binder, is particles bound by the binders of the present invention.

An example of densification using one of the polymeric binders of the present invention is given below:

EXAMPLE XI

A 50 gram amount of polypropylene glycol is diluted with 50 grams deionized water. The resulting solution is sprayed on 321 grams of an intrafiber crosslinked cellulose fluff (HBA from Weyerhaeuser Company of Tacoma, Wash.) that was air entrained in a blender like mixing device. While the HBA fiber is still damp, 438 grams of IM 1000F (supplied by Hoechst-Celanese, of Portsmouth, Va.) is added to the mixture. The resultant mixture is then vacuumed from the blender and spread on a counter to dry overnight. Then 550 gram/square meter handsheets, six inches in diameter, are made in a laboratory padformer. Those pads are then pressed at 2000 and 3000 psi (or 60 and 90 pli in a calendar roll), respectively, to yield sheets with densities of 0.3 and 0.5 g/cc. Alternatively, pads of untreated HBA blended with 45% IM 1000F would require heating to 100° C. and pressures between 8,000 and 11,000 psi to produce pads of similar densities.

Particulate Binding

FIG. 13 shows an isolated, enlarged cellulose fiber 600 with SAP particles 602 bound to it by a binder of the present invention. This drawing illustrates an example of the SAP retaining its discrete particulate form following binding to the fibers. Some particle to particle fusion may occur in accordance with this invention, but maintenance of a discrete particulate form excludes formation of a completely confluent film in which the particles lose their particulate identity. Such a confluent film produces gel blocking that interferes with efficient liquid absorption into the fibers.

The shown fiber 600 is elongated, and has an aspect ratio (ratio of length to width) of about 10:1, or in the range 10:1 to 5:1.

FIG. 14 shows the particles 602 distributed substantially uniformly throughout the depth 604 of a pad 606. The particles are also shown adhering to all the surfaces of the pad. Particles may be distributed in any desired pattern throughout the pad in accordance with this invention, and need not necessarily adhere to all surfaces or be distributed throughout the volume of the mat, or distributed uniformly.

Fiber Mixtures

The fibers of the present invention, such as fiber 600, can be mixed with other types of fibers, such as that disclosed in U.S. Pat. No. 5,057,166 which is incorporated herein by reference in its entirety. The latex coated fibers of that patent can be mixed with the fibers of the present invention to produce an absorbent product that has characteristics of both types of fibers.

Additional Binder Characteristics

U.S. Pat. No. 3,903,889 discloses a process for adhering absorbent particles to pulp fibers using syrup, honey, and other polysaccharides such as dextrins. An essential requirement of these adhesive agents is that they must possess the property of being permanently pliable, and not rigidizing into a brittle film. The binders of the present invention, in contrast, are capable of functioning as a binder after solidifying into a rigid crystalline material. Even the binders of the present invention that do not rigidify into a solid (such as glycerin, low molecular weight PEG (below about 4000 g/mole) and PPG) are very hygroscopic, and can be present on fibers having a total water content of no more than 15%, or even 12%. This is in contrast to the adhesives such as honey and corn syrup disclosed in U.S. Pat. No. 3,903,889 that are not hygroscopic. Polysaccharides (such as corn syrup, honey and dextrins) are excluded as binders from some embodiments of the invention because they are a fertile substrate for microbial growth.

Having illustrated and described the principles of the invention in many preferred embodiments, it should be apparent to those skilled in the art that the invention can be modified in arrangement and detail without departing from such principles. We claim all modifications coming within the spirit and scope of the following claims.

We claim:

1. A fibrous product comprising:
    fibrous material comprising fibers having a hydrogen bonding functionality;
    superabsorbent particles having a hydrogen bonding or a coordinate covalent bonding functionality; and
    a polymeric binder selected from the group consisting of poly(caprolactone) diol, polyamides and polyamines, wherein the polymeric binder has on each repeating unit of the polymeric binder a functional group capable of forming a hydrogen bond or a coordinate covalent bond with the particles, or a hydrogen bond with the fibers, and wherein the binder has formed hydrogen bonds with the fibers and hydrogen bonds or coordinate covalent bonds with the particles, whereby a substantial portion of the particles are adhered to the fibers in particulate form by the binder to the fibrous material by non-covalent bonds.

2. The product of claim 1 wherein the fibrous material comprises cellulosic fibers.

3. The product of claim 2 wherein the cellulosic fibers are in the form of a web or sheet.

4. The product of claim 1 wherein the binder is present in an amount of from about 3 to 80 percent of the total weight of the fibrous material, binder and particles.

5. The product of claim 4 wherein the binder is present in an amount of from about 3 to 40 percent of the total weight of the fibrous material, binder and particles.

6. The product of claim 5 wherein the binder is present in an amount of from about 3 to 25 percent of the total weight of the fibrous material, binder and particles.

7. The product of claim 1 wherein the particles are present in an amount of 0.05 to 80 percent of the total weight of the fibrous material, binders and particles.

8. The product of claim 1 wherein the particles are bound to the binder hydrogen bonds, and the binder is bound to the fibers by hydrogen bonds.

9. The product of claim 1 wherein the binder is selected from the group consisting of polyamides and polyamines.

10. The product of claim 9 wherein the binder is a polypeptide.

11. The product of claim 1 further comprising latex coated fibers.

12. The product of claim 1 wherein the particles are bound to the binder by coordinate covalent bonds, and the binder is bound to the fibers by hydrogen bonds.

13. An absorbent article comprising the product of claim 1.

14. An absorbent composite product comprising:
    a fibrous cellulosic web comprising cellulosic fibers having a hydrogen bonding functionality;
    superabsorbent particles having a hydrogen bonding or coordinate covalent bonding functionality;
    a polymeric binder selected from the group consisting of poly(caprolactone) diol, polyamides, and polyamines, wherein the polymeric binder has on each repeating unit of the polymeric binder, a functional group capable of forming a hydrogen bond or a coordinate covalent bond with the particles, or a hydrogen bond with the fibers, and wherein the binder has formed hydrogen bonds with the fibers and hydrogen bonds or coordinate covalent bonds with the particles, whereby a substantial portion of the particles are adhered to the fibers by the binder through said bonds, the composite product comprising 3–80 percent binder and 5–80 percent particles in solid particulate form, by weight of the total weight of the fibrous material, binder and particles.

15. A fibrous product comprising:
    fibrous material comprising fibers that have a hydrogen binding functionality;
    a polymeric binder on the fiber in a sufficient amount to bind a superabsorbent particle to the fiber, the binder selected from the group consisting of poly(caprolactone) diol, polyamides, and polyamines, wherein the polymeric binder has on each repeating unit of the polymeric binder a functional group capable of forming hydrogen bonds or coordinate covalent bonds with the particles, or hydrogen bonds with the fibers.

16. A fibrous product made by the method, comprising the steps of:
provid ing fibrous material comprising a fiber having a hydrogen bonding functionality;
providing superabsorbent particles having a hydrogen bonding or a coordinate covalent bonding functionality;
selecting a polymeric binder having a hydrogen bonding functionality or coordinate covalent bond forming functionality on each repeating unit of the polymeric binder, the binder being selected from the group consisting of poly(caprolactone) diol, polyamides and polyamines; and
providing the binder in a sufficient amount in the presence of the fibers to bind the binder to at least a portion of the particles by a hydrogen bond or coordinate covalent bond, and to bind the binder to the fibers by a hydrogen bond under conditions that favor formation of non-covalent bonds wherein the particles are insoluble in the binder.

17. The fibrous product of claim 16 wherein the providing step comprises applying the binder to the fibers, then applying the particles to the fibers and binder.

18. The fibrous product of claim 16 wherein the providing step comprises applying the particles to the fibers, then applying the binder to the particles and the fibers.

19. The fibrous product of claim 16 wherein the providing step comprises simultaneously applying the binder and the particles to the fibers.

20. The fibrous product of claim 16 wherein the binder and particles are selected to bind the binder to the particles by hydrogen bonds.

21. The fibrous product of claim 16 wherein the fibers comprise cellulosic fibers.

22. The fibrous product of claim 21 wherein the cellulosic fibers comprise a cellulosic web or loose cellulosic fibers, and the binding step further comprises applying the binder to the web or loose fibers.

23. The fibrous product of claim 22 wherein the binding step comprises applying the binder to the web or loose cellulosic fibers and subsequently applying the particles to the web or loose fibers.

24. The fibrous product of claim 22 wherein the binding step comprises providing the particles to the web or loose fibers and subsequently applying the binder to the web or loose fibers.

25. The fibrous product of claim 22 wherein the binding step comprises providing the particles to the web or loose fibers separately but simultaneously with the step of applying the binder to the web or loose fibers.

26. The fibrous product of claim 21 wherein the particles are bound to the fibers in the absence of substantial intrafiber bonding.

27. The fibrous product of claim 21 further comprising the step of densifying the cellulosic fibers by external application of pressure following the binding step.

28. The fibrous product of claim 27 wherein the densifying step comprises densifying the cellulosic fiber to a density of about 0.1 to 0.7 g/cc.

29. The fibrous product of claim 29 wherein the densifying step comprises densifying the cellulosic fiber to a density of about 0.1 to 0.3 g/cc.

30. The fibrous product of claim 16 wherein the fibers comprise synthetic or natural fibers having a hydrogen bonding functional group.

31. The fibrous product of claim 30 wherein the synthetic fibers are selected from the group consisting of rayon, nylon, polyester and polyamide fibers.

32. The fibrous product of claim 16 wherein the polymeric binder has a molecular weight greater than 500 grams/mole.

33. The fibrous product of claim 32 wherein the polymeric binder has a molecular weight greater than 4000 grams/mole.

34. The fibrous product of claim 33 wherein the polymeric binder has a molecular weight less than 8000 grams/mole.

35. The fibrous product of claim 16 wherein the binder is present in the treated product in an amount of at least 3 percent by weight.

36. The fibrous product of claim 35 wherein the binder is present in the treated product in an amount of no more than 40 percent by weight.

37. The fibrous product of claim 16 wherein the particles are bound to the fibers at a temperature of less than 150° C.

38. The fibrous product of claim 37 wherein the particles are bound to the fibers without external application of heat.

39. The fibrous product of claim 16 wherein the binder is a solid particulate and the fibers contain at least 7% water by weight when the binding step is performed.

40. The fibrous product of claim 16 wherein the binder is a liquid binder and the fibers contain at least 0.5 percent water by weight when the binding step is performed.

41. The fibrous product of claim 16 wherein the binder is a thermoplastic binder which is a solid at room temperature, and the binding step further comprises elevating the thermoplastic binder above its melting temperature to melt the thermoplastic binder and thermoplastically bind the fibers to each other and the fibers to the particles.

42. The fibrous product of claim 16 further comprising providing a second binder that is a thermoplastic binder which is a solid at room temperature, and the binding step further comprises applying the second binder to the fibers and elevating the thermoplastic binder above its melting temperature to melt the thermoplastic binder and thermoplastically bind the fibers to each other and the fibers to the particles.

43. The fibrous product of claim 42 wherein the second binder is applied to the fibers and the temperature elevated after the particles have been bound to the fibers by the binder that has hydrogen bonding or coordinate covalent bonding functionalities.

44. The fibrous product of claim 42 wherein the second binder is applied to the fibers before the particles are provided in the presence of the fibers.

45. The fibrous product of claim 42 wherein the second binder contains a hydrogen bonding functionality which hydrogen bonds to the fibers and particles.

46. The fibrous product of claim 42 wherein the second binder is applied to the fibers before the binder that has hydrogen bonding or coordinate covalent bonding functionalities is applied to the fibers.

47. The fibrous product of claim 16 wherein the binder and particles form hydrogen bonds to bind the binder and particles together.

48. The fibrous product of claim 16 wherein the binder and particles form coordinate covalent bonds that bind the binder and particles together.

49. The fibrous product of claim 16 wherein the binding step comprises applying the binder to the fibers, and subsequently activating the binder to bind the particles to the binder and the binder to the fibers.

50. The fibrous product of claim 49 wherein the binder is applied to the fibers as a solid, and the step of activating the binder comprises applying a liquid to the fibers alter applying the binder to the fibers.

51. The fibrous product of claim 49 wherein the binder is activated by heating the fibers alter applying the binder to the fibers.

52. The fibrous product of claim 51 wherein the binder is activated, by heating the fibrous material, and the particles are applied tot he fibrous material in a pattern that corresponds to a desired distribution of particles in the fibrous material.

53. The fibrous product of claim 49 wherein the binder is activated by applying kinetic energy to the fibers alter applying the binder to the fibers.

54. The fibrous product of claim 53 wherein the step of applying kinetic energy comprises mechanically agitating the fibers.

55. The fibrous product of claim 49 wherein the binder is applied to the fibers as a liquid and allowed to dry, and the step of activating the binder comprises the step of applying a reactivation liquid to the fibers alter the liquid has dried.

56. The fibrous of claim 55 wherein the reactivation liquid is applied to the fibrous material in a pattern that corresponds to a desired distribution of particles in the fibrous material.

57. The fibrous product of claim 49 wherein the step of activating the binder comprises activating the binder in a pattern that corresponds to a desired distribution of particles in the fibrous material.

58. The fibrous product of claim 49 wherein the binder is activated, then the particles are applied to the fibers while the binder is in an activated state.

59. The fibrous product capable of adhering superabsorbent particles, made by the method comprising the steps of:

providing fibers that contain a hydrogen bonding functionality;

applying to the fibers an amount of a binder sufficient to bind superabsorbent particles to the fibers, wherein the binder is selected from the group consisting of poly(caprolactone) diol, polyamides and polyamines, wherein the polymeric binder has on each repeating unit of the polymeric binder a functional group capable of forming a hydrogen bond.

60. The fibrous product of claim 59 wherein the fiber comprises a cellulosic fiber.

61. An absorbent cellulose fiber product, made by the method comprising the steps of:

forming a cellulosic fiber web having a moisture content of at least 0.5 percent by weight;

providing superabsorbent particles in contact with the web; and applying to the web 3–80 percent by weight of a binder selected from the group consisting of poly(caprolactone) diol, polyamides and polyamines, wherein each repeating unit of the polymeric binder has a hydrogen bonding functionality.

* * * * *

UNITED STATES PATENT AND TRADEMARK OFFICE
CERTIFICATE OF CORRECTION

PATENT NO. : 5,543,215
DATED : August 6, 1996
INVENTOR(S) : M.R. Hansen et al.

It is certified that error appears in the above-indentified patent and that said Letters Patent is hereby corrected as shown below:

| COLUMN | LINE | |
|---|---|---|
| [56] | Refs. Cited | "Properites*" should read --Properties*-- |
| [56] | Refs. Cited | "Hogue et al.," should read --Hoque et al.,-- |
| [56] | Refs. Cited Item 13) | "Sliwiok an Kowalska," should read --Sliwiok and Kowalska,-- |
| [56] | Attorney, Agent | After "O'Connor" delete --;-- |
| 3 | 46 | After "(e.g." insert --,-- |
| 6 | 58 | "is" should read --1$s$-- |
| 6 | 60 | "Is" should read --1$s$-- |
| 9 | 15 | After "i.e." insert --,-- |

UNITED STATES PATENT AND TRADEMARK OFFICE
CERTIFICATE OF CORRECTION

PATENT NO. : 5,543,215
DATED : August 6, 1996
INVENTOR(S) : M.R. Hansen et al.

It is certified that error appears in the above-indentified patent and that said Letters Patent is hereby corrected as shown below:

| COLUMN | LINE | |
|---|---|---|
| 10 (TABLE I) | 13 | "Antiacme" should read --Antiacne-- |
| 11 | 53 | Eliminate the space between "diimino-" and "2, 4, . . ." |
| 13 | 51 | After "i.e." insert --,-- |
| 14 | 34 | "interefere" should read --interfere-- |
| 14 | 36 | After "(e.g." insert --,-- |
| 15 | 13 | "infrafiber" should read --intrafiber-- |
| 16 | 40 | "a especially" should read --an especially-- |
| 17 | 58-59 | "St. Louis, Mis.)" should read --St. Louis, Missouri or Mo.)-- |
| 19 | 59 | "hold" should read --hole-- |
| 20 | 10 | "(IM 10000F;" should read --(IM 1000F;-- |
| 20 | 33 | After "materials" insert --:-- |
| 20 | 56-57 | Insert line space between "polyimides" and "In addition, . . ." |
| 21 | 11 | After first occurrence of "material" insert --. The thermoset-- |

UNITED STATES PATENT AND TRADEMARK OFFICE
CERTIFICATE OF CORRECTION

PATENT NO. : 5,543,215

DATED : August 6, 1996

INVENTOR(S) : M.R. Hansen et al.

It is certified that error appears in the above-indentified patent and that said Letters Patent is hereby corrected as shown below:

| COLUMN | LINE | |
|---|---|---|
| 26 (Claim 8, | 28 line 2) | "binder hydrogen" should read --binder by hydrogen-- |
| 26 (Claim 15, | 63 line 3) | "binding" should read --bonding-- |
| 27 (Claim 26, | 54 line 2) | "intrafiber" should read --interfiber-- |
| 27 (Claim 29, | 62 line 1) | "claim 29 wherein" should read --claim 28 wherein-- |
| 29 (Claim 50, | 1 line 3) | "alter" should read --after-- |
| 29 (Claim 51, | 4 line 2) | "alter" should read --after-- |
| 29 (Claim 52, | 7 line 2) | After "activated" delete --,-- |
| 29 (Claim 52, | 8 line 3) | "tot he" should read --to the-- |

UNITED STATES PATENT AND TRADEMARK OFFICE
CERTIFICATE OF CORRECTION

PATENT NO. : 5,543,215
DATED : August 6, 1996
INVENTOR(S) : M.R. Hansen et al.

It is certified that error appears in the above-indentified patent and that said Letters Patent is hereby corrected as shown below:

COLUMN     LINE

| COLUMN | LINE | |
|---|---|---|
| 29 (Claim 53, | line 2) | "alter" should read --after-- |
| 29 (Claim 55, | line 4) | "alter" should read --after-- |
| 29 (Claim 56, | line 1) | After "fibrous" insert --product-- |
| 30 (Claim 59, | line 1) | "The fibrous product" should read --A fibrous product-- |

Signed and Sealed this

Twentieth Day of May, 1997

Attest:

BRUCE LEHMAN

*Attesting Officer*     *Commissioner of Patents and Trademarks*